US012582350B1

(12) United States Patent
Shamain et al.

(10) Patent No.: US 12,582,350 B1
(45) Date of Patent: Mar. 24, 2026

(54) RESPIRATION WAVEFORM GENERATION FOR SLEEP STAGE ESTIMATION IN A CONTACTLESS MANNER USING MILLIMETER WAVE RADAR

(71) Applicant: Amazon Technologies, Inc., Seattle, WA (US)

(72) Inventors: Durgaprasad Kashinath Shamain, Los Gatos, CA (US); Amit Kachroo, San Jose, CA (US); Morris Yuanhsiang Hsu, Mountain View, CA (US)

(73) Assignee: Amazon Technologies, Inc., Seattle, WA (US)

( * ) Notice: Subject to any disclaimer, the term of this patent is extended or adjusted under 35 U.S.C. 154(b) by 313 days.

(21) Appl. No.: 17/983,063

(22) Filed: Nov. 8, 2022

Related U.S. Application Data

(60) Provisional application No. 63/410,567, filed on Sep. 27, 2022.

(51) Int. Cl.
*A61B 5/00* (2006.01)
*A61B 5/05* (2021.01)
*G01S 7/292* (2006.01)
*G01S 13/88* (2006.01)

(52) U.S. Cl.
CPC .............. *A61B 5/4812* (2013.01); *A61B 5/05* (2013.01); *A61B 5/7203* (2013.01); *A61B 5/7246* (2013.01); *G01S 7/2927* (2013.01); *G01S 13/88* (2013.01)

(58) Field of Classification Search
CPC .... A61B 5/4812; A61B 5/4806; A61B 5/4815
See application file for complete search history.

(56) References Cited

U.S. PATENT DOCUMENTS

| | | | |
|---|---|---|---|
| 2006/0009704 A1* | 1/2006 | Okada .................. | A61B 5/1135 600/534 |
| 2009/0192556 A1* | 7/2009 | Wu ........................ | A61B 5/1116 607/3 |
| 2021/0398666 A1* | 12/2021 | Maslik ................. | A61B 5/4842 |
| 2022/0233079 A1* | 7/2022 | Park .................... | A61B 5/7239 |
| 2023/0263465 A1* | 8/2023 | Jorge ................. | A61B 5/02405 600/301 |

* cited by examiner

*Primary Examiner* — Anh Tuan T Nguyen
*Assistant Examiner* — Tommy T Ly
(74) *Attorney, Agent, or Firm* — Eversheds Sutherland (US) LLP

(57) ABSTRACT

A computing device for monitoring a sleep stage of a user in a contactless manner includes a processor, a radar unit, and a memory. The processor executes instructions from memory to cause the computing device to perform a series of signal processing methodologies on the waveforms received from the radar unit to accurately determine the sleep stage of the user in a contactless manner.

17 Claims, 20 Drawing Sheets

_400

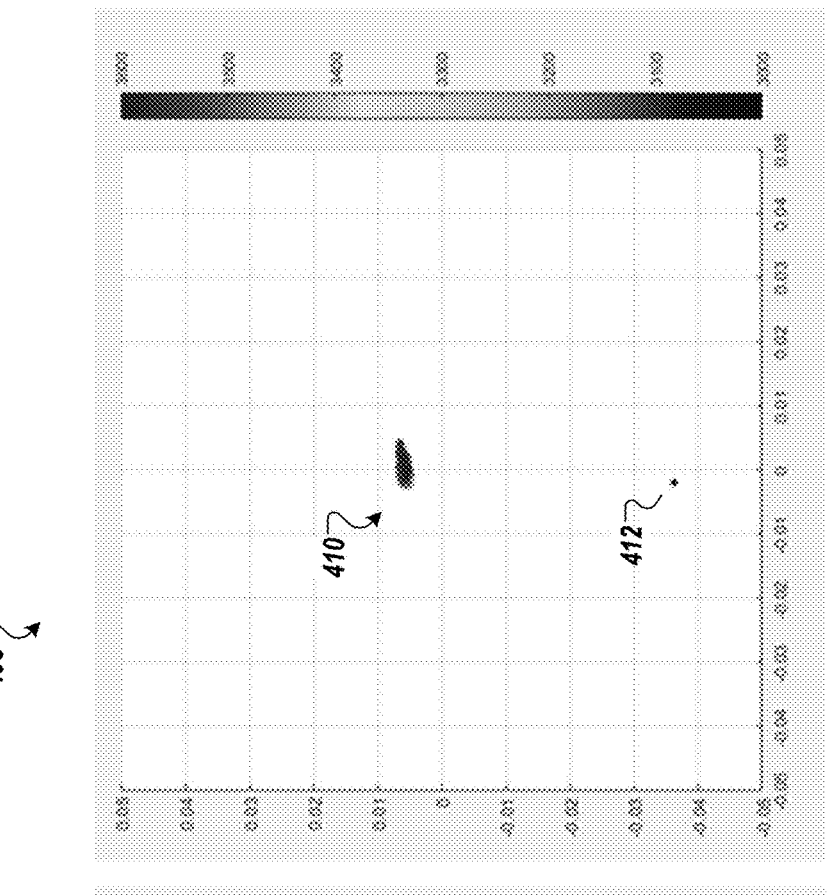
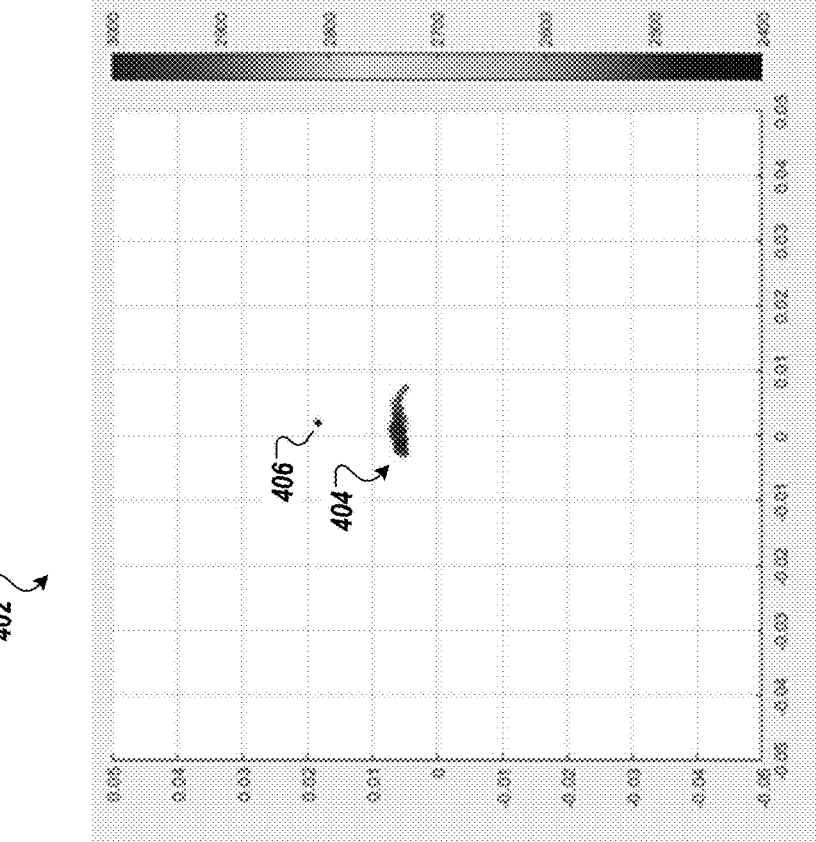
FIG. 4B

600

1240

1242

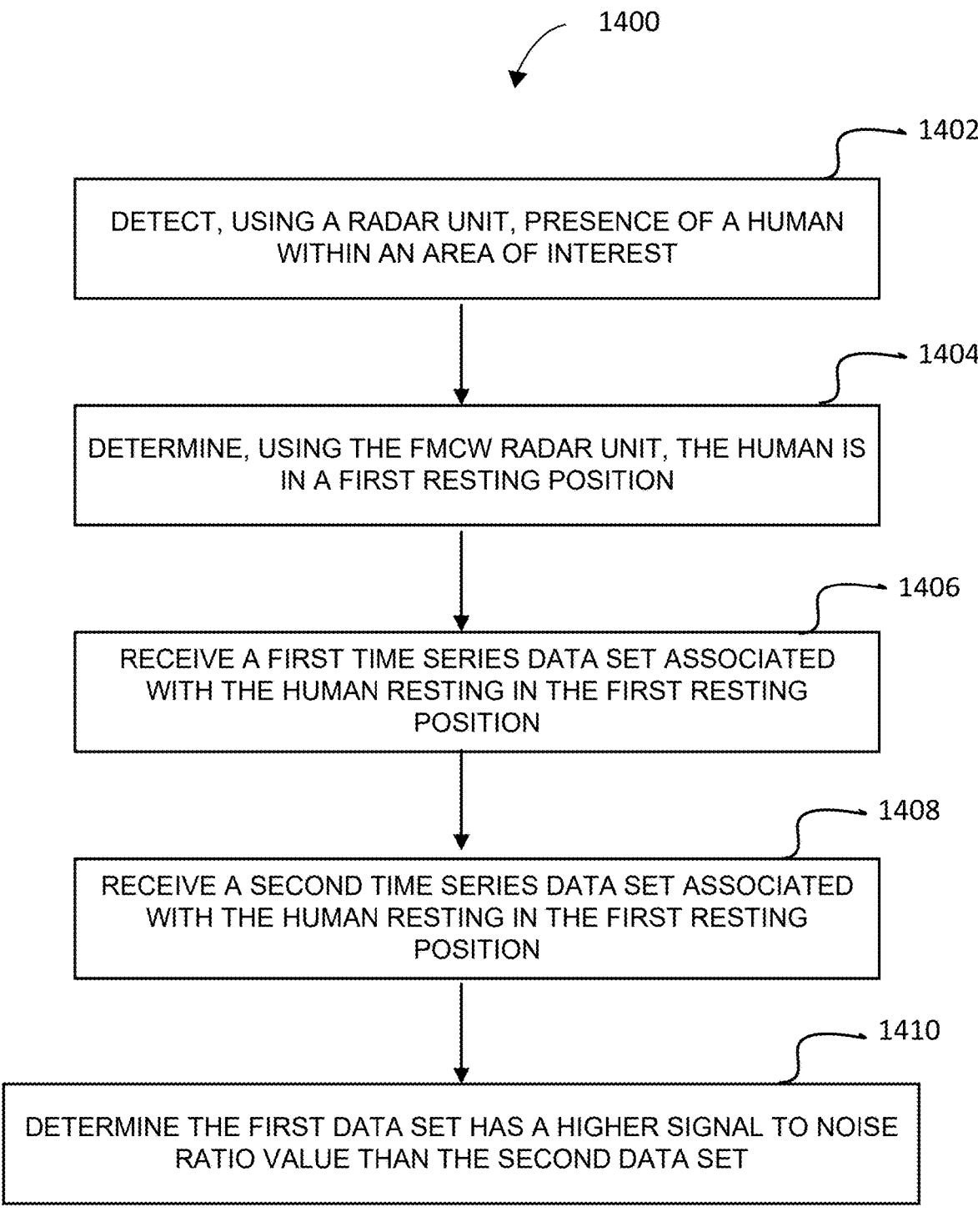

1400

1402

DETECT, USING A RADAR UNIT, PRESENCE OF A HUMAN WITHIN AN AREA OF INTEREST

1404

DETERMINE, USING THE FMCW RADAR UNIT, THE HUMAN IS IN A FIRST RESTING POSITION

1406

RECEIVE A FIRST TIME SERIES DATA SET ASSOCIATED WITH THE HUMAN RESTING IN THE FIRST RESTING POSITION

1408

RECEIVE A SECOND TIME SERIES DATA SET ASSOCIATED WITH THE HUMAN RESTING IN THE FIRST RESTING POSITION

1410

DETERMINE THE FIRST DATA SET HAS A HIGHER SIGNAL TO NOISE RATIO VALUE THAN THE SECOND DATA SET

FIG. 14A

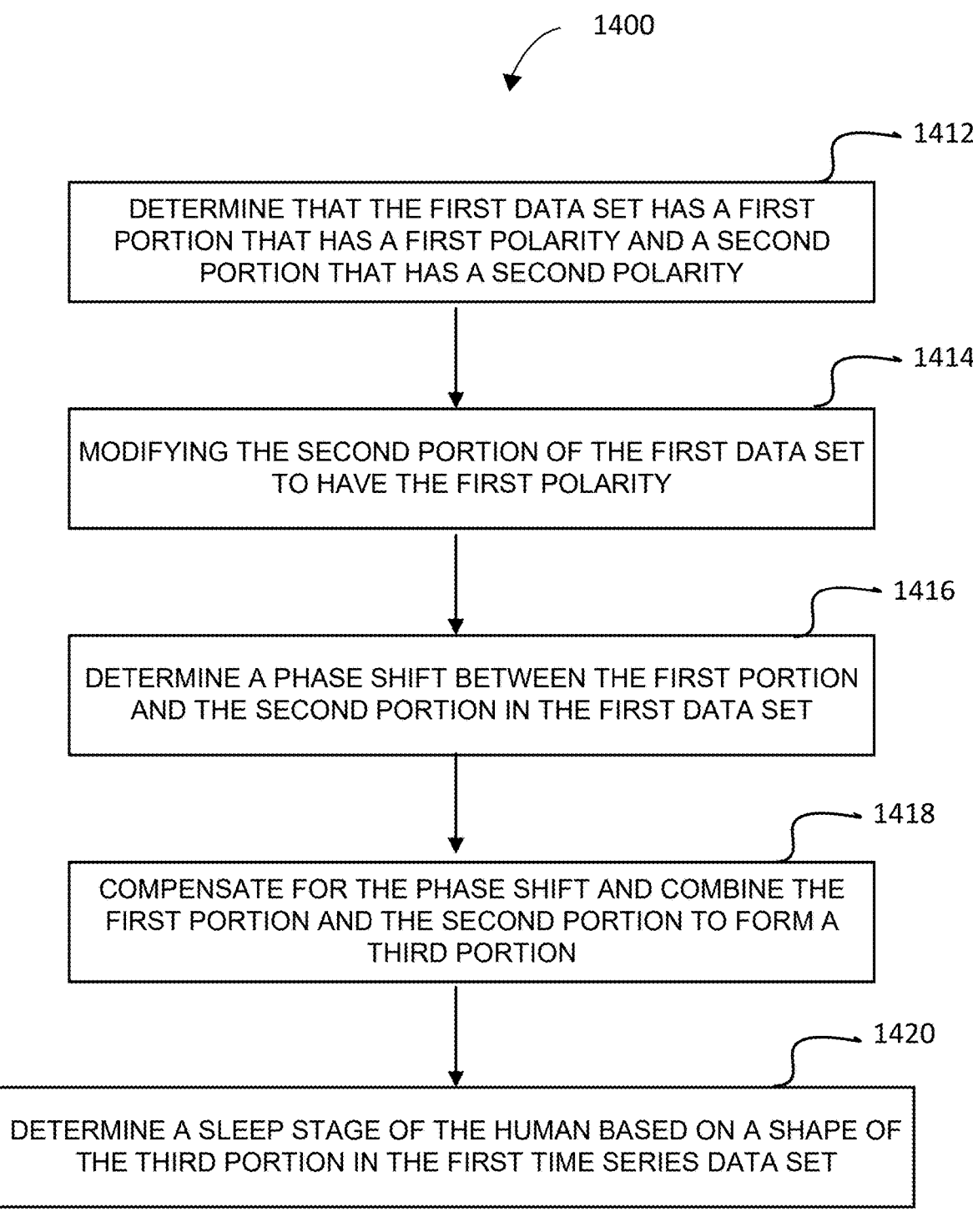

1400

1412

DETERMINE THAT THE FIRST DATA SET HAS A FIRST PORTION THAT HAS A FIRST POLARITY AND A SECOND PORTION THAT HAS A SECOND POLARITY

1414

MODIFYING THE SECOND PORTION OF THE FIRST DATA SET TO HAVE THE FIRST POLARITY

1416

DETERMINE A PHASE SHIFT BETWEEN THE FIRST PORTION AND THE SECOND PORTION IN THE FIRST DATA SET

1418

COMPENSATE FOR THE PHASE SHIFT AND COMBINE THE FIRST PORTION AND THE SECOND PORTION TO FORM A THIRD PORTION

1420

DETERMINE A SLEEP STAGE OF THE HUMAN BASED ON A SHAPE OF THE THIRD PORTION IN THE FIRST TIME SERIES DATA SET

FIG. 14B

RESPIRATION WAVEFORM GENERATION FOR SLEEP STAGE ESTIMATION IN A CONTACTLESS MANNER USING MILLIMETER WAVE RADAR

RELATED APPLICATION

This application claims the benefit of U.S. Provisional Application No. 63/410,567, filed Sep. 27, 2022, the entire content of which is incorporated by reference herein.

BACKGROUND

Millimeter wave (mmWave) is a special class of radar technology that uses short wavelength electromagnetic waves. Radar systems transmit electromagnetic wave signals that objects in their path then reflect. By capturing the reflected signal, a radar system can determine the range, velocity, and angle of the objects. mm Wave radars transmit signals with a wavelength that is in the millimeter range. This is considered a short wavelength in the electromagnetic spectrum and is one of the advantages of this technology. Indeed, the size of system components, such as the antennas required to process mmWave signals, is small. Another advantage of short wavelengths is the high accuracy. A mmWave system operating at 30-300 GHz can have the ability to detect movements that are as small as a fraction of a millimeter.

BRIEF DESCRIPTION OF DRAWINGS

The present inventions will be understood more fully from the detailed description given below and from the accompanying drawings of various embodiments of the present invention, which, however, should not be taken to limit the present invention to the specific embodiments, but are for explanation and understanding only. These drawings include the following figures, in which like numerals indicate like parts:

FIG. 4B illustrates a first graph with the current segment offset from a previous circle center and a second graph with the current segment offset from a current circle center, according to at least one embodiment.

FIGS. 14A and 14B show example steps in bin selection and inversion compensation in a method for monitoring a sleep stage of a human in a contactless manner, according to at least one embodiment.

DETAILED DESCRIPTION

Figure 1A:
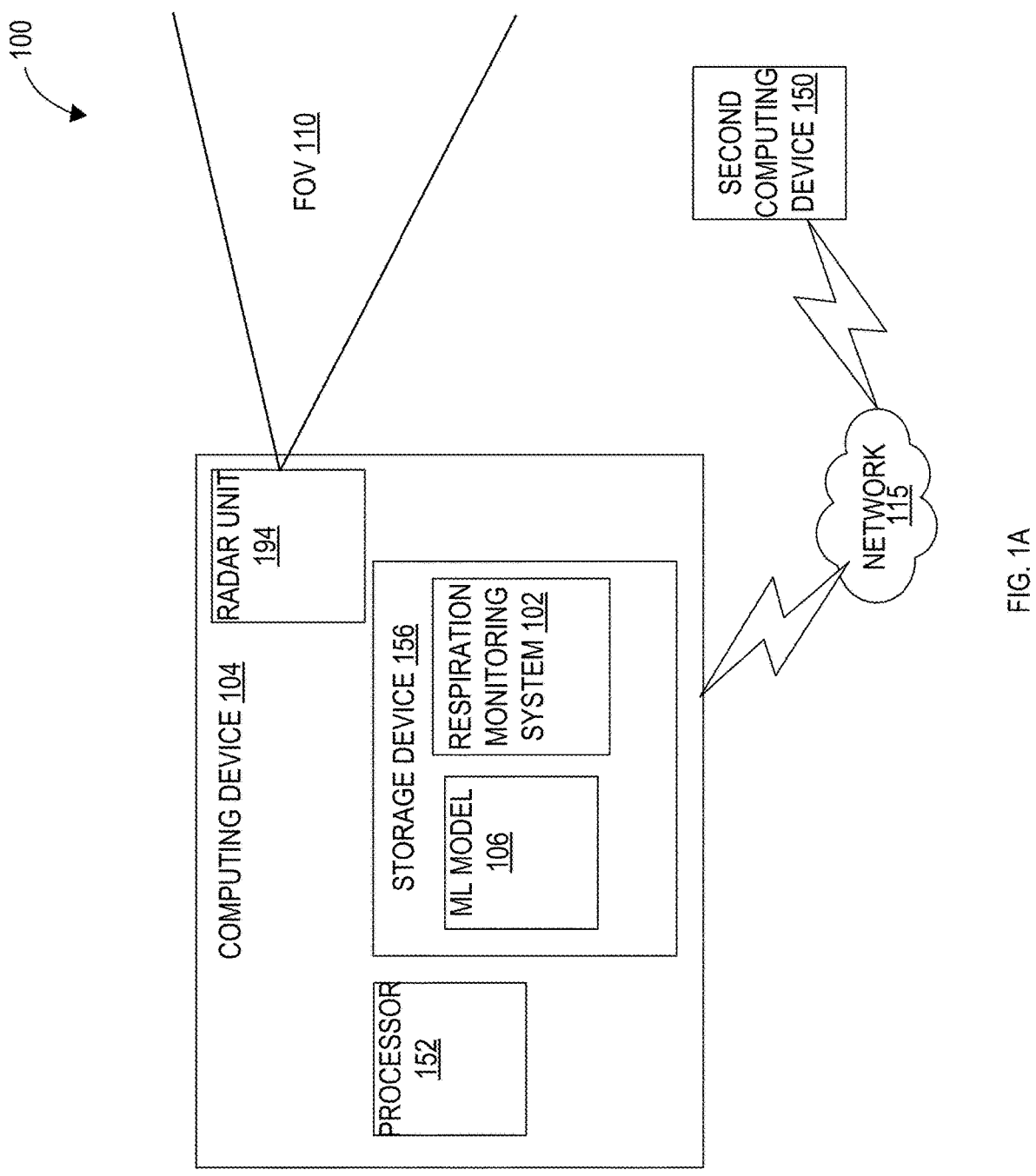
FIG. 1A is a block diagram of a system for generating a respiration waveform from radar data for estimating a sleep stage of a human in a contactless manner, according to at least one embodiment.

While some research papers have demonstrated using mmWave radar to capture respiration rate, very few have tried to create the actual respiration waveform (also referred to as breathing waveform), and none account for practical respiration estimation in a real environment. For example, the user would not be facing the radar because people sleep in different positions, and can change position throughout the night, or there can be multiple people in the bed. Although these conventional mmWave radar systems can capture the respiration rate, these systems do not generate an actual breathing waveform itself, failing to account for different sleeping positions, a user changing positions, multiple users within the space, or the like in realistic sleep environments.

Aspects and embodiments of the present disclosure can overcome these challenges and others by providing respiration waveform generation for sleep stage estimation in a contactless manner. Aspects and embodiments of the present disclosure can provide end-to-end flow to use radar data to recreate a respiration waveform as would be seen by a chest belt under realistic sleep environments. Aspects and embodiments of the present disclosure can recover breathing waveforms using circle stitching with angular inversion compensation, bin selecting, inversion compensation, segmentation, and DC wandering correction. Aspects and embodiments of the present disclosure can be used in sleep monitoring (e.g., assessing the sleep quality from the motion and respiratory patterns) using smart-home IoT devices, such as voice-assistant devices, tablets, or the like. Aspects and embodiments of the present disclosure can provide a computing device for estimating sleep stage of a human in a contactless manner. The computing device includes a processor, a radar unit, and a memory. The radar unit includes a mmWave transmitter (TX) and a receiver (RX). The radar unit generates and transmits electromagnetic wave signals that objects in their path then reflect. By capturing the reflected signal, a radar unit can determine the range, velocity, and angle of the objects. mmWave radar units transmit signals with a wavelength that is in the millimeter range. A mmWave radar unit can operate at 30-300 GHz and can have the ability to detect movements that are as small as a fraction of a millimeter. Aspects and embodiments of the present disclosure can also be used in connection with a continuous positive airway pressure (CPAP) machine. For example, the computing device can communicate with the CPAP machine or be integrated within the CPAP machine. Aspects and embodiments of the present disclosure can detect apneas or other breathing interruptions that can be useful inputs to a CPAP machine or other devices.

Devices may measure a variety of motions and vibrations such as a person's breathing in order to determine a person's sleep stage. The propagation of radar waves that encounter a person or object may reflect due to the presence of the person (e.g., a person inhaling and exhaling) or object, and the detection of the reflected radar waves may result in a waveform that represents the person's breathing, and which may be analyzed to determine a person's sleep stage. The radar data can include information about the reflected power at various distances. The radar data can include information about the range, motion, velocity, and angle of a detected object. The computing device detects the presence of a human within an area of interest, and determines that the human is in a first resting position. The computing device performs a series of signal processing methodologies on the waveforms received from the radar unit to recreate a respiration waveform that can be used in connection with a trained ML model to accurately determine the sleep stage of a human in a contactless manner. The computing device may use a trained ML model to accurately determine the sleep stage of a human in a contactless manner. The trained ML model can be trained using supervised or unsupervised training techniques. The trained ML model can be trained using respiration data collected from a polysomnography (PSG) chest belt used in sleep labs. The trained ML model can be a sleep stage estimation ML model. During inference, the computing device can measure and use radar data to generate a respiration waveform that is input into the trained ML model, instead of data from a PSG chest belt. While the approach of using existing chest belt data reduces complexity in the data collection requirement for creating the ML model, aspects and embodiments of the present disclosure can reliably reproduce the respiration waveform that would be measured by a chest belt to be input into the trained ML model to estimate the sleep stage.

It should be noted that various embodiments are described below with respect to mmWave radar. In other embodiments, other sensing with 3D positional capabilities, but without the capability to directly identify a person can be used. For example, ultrasound, lidar, or the like can be used in connection with the various embodiments described herein.

FIG. 1A is a block diagram of a system 100 for generating a respiration waveform from radar data for estimating a sleep stage of a human in a contactless manner, according to at least one embodiment. The system 100 may include a computing device 104, which may be a smart-home IoT device, such as a voice-assistant device, a network 115 (e.g., WLAN, a wide area network (WAN), or cellular), and an optional second computing device 150. In at least one embodiment, the computing device 104 includes a radar unit 194, a processor 152, and a storage device 156. The storage device 156 can store a machine learning (ML) model 106 and a respiration monitoring system 102. In another embodiment, the respiration monitoring system 102 can be processing logic comprising hardware, software, firmware, or any combination thereof.

The computing device 104 may be located in a room (or other space) in a building in order to detect one or more users in the presence within the room (or other space) using the radar unit 194. In at least one embodiment, the radar unit 194 includes a mmWave TX and RX. The radar unit 194 generates and transmits electromagnetic wave signals that objects in their path then reflect. By capturing the reflected signal, a radar unit 194 can determine the range, velocity, and angle of the objects. The radar unit 194 can provide the radar data (time-series data sets) to the processor 152 for processing by the respiration monitoring system 102 to generate the respiration waveform, as described in more detail below. Once the respiration waveform has been generated, it can be used as an input to the ML model 106 to infer a sleep stage of the user, as described in more detail below.

In at least one embodiment, the respiration monitoring system 102 collects and processes radar unit data (e.g., point cloud data) to generate a respiration waveform as described in detail below to be input into the ML model 106 to make an inference of a sleep stage of a user within a spatial region surrounding the computing device 104. A "waveform" as used in this disclosure refers to time series data obtained from one or more spatial regions (e.g., an area of interest) in the field of view of the radar unit. A respiration waveform can be an identified waveform corresponding to the respiration of a user within the spatial region. In at least one embodiment, the computing device 104 uses the ML model 106 to estimate a sleep stage of a user within a spatial region surrounding the computing device 104. In another embodiment, the respiration monitoring system 102 can collect and process radar data so that not all of the radar data needs to be stored at the computing device 104 or transmitted to the computing device 150. In at least one embodiment, the respiration monitoring system 102 can collect and process the radar data (e.g., point cloud data) so that only the radar data that helps infer sleep stages is stored at the computing device 104. In another embodiment, the respiration monitoring system 102 can transmit the radar data or the respiration waveform to the second computing device 150 to process the radar data to generate the respiration waveform and/or make an inference of the sleep stage using the respiration waveform. In some embodiments, the computing device 104 can operate in various frequency bands, such as 2.45 GHZ, 5 GHZ, 6 GHZ, cellular frequency bands (e.g., LTE, 4G), or the like, to communicate with the second device 150 over the network 115.

In various embodiments, the computing device 104 may receive radar data from the radar unit 194 to generate a respiration waveform of a human if present in the spatial region of the computing device and estimate a sleep stage based on the respiration waveform. This estimation, as mentioned, may be performed using a trained ML model, such as a support vector machine (SVM) model, a neural network (NN) model, or another trained ML model.

In other embodiments, the second computing device 150 can be a cloud controller used in connection with the respiration monitoring system 102 and the ML model 106 at the computing device 104. The computing device 150, located in the cloud across the network 115, may perform the initial training of an ML model, which then can be deployed as the ML model 106. The computing device 150 can also include a respiration monitoring system that is similar to the respiration monitoring system 102. In at least one embodiment, the respiration monitoring system 102 can send data to the respiration monitoring system at the second computing device for signal processing when the computing device 104 has limited storage and computing resources, for example. The respiration monitoring system 102 can be a sub-process or companion application of the respiration monitoring system at the second computing device. Alternatively, the respiration monitoring system can be the same as the respiration monitoring system 102.

In at least one embodiment, the computing device 150 may include, for example, the processor 152 and storage device 156. The storage device 156, which may be understood to include computer memory and/or storage, may include a ML model 160, a respiration monitoring system 102. Training data can be data collected by a chest belt and trained by the second computing device 150. In one embodiment, the ML model 160 may include known waveforms associated with different sleep stages (e.g., wake, light, deep, or rapid eye movement (REM)) to identify which sleep stage the user is in currently. The training data may later be updated over time and can be used to update or retrain the ML model 106.

Figure 1B:
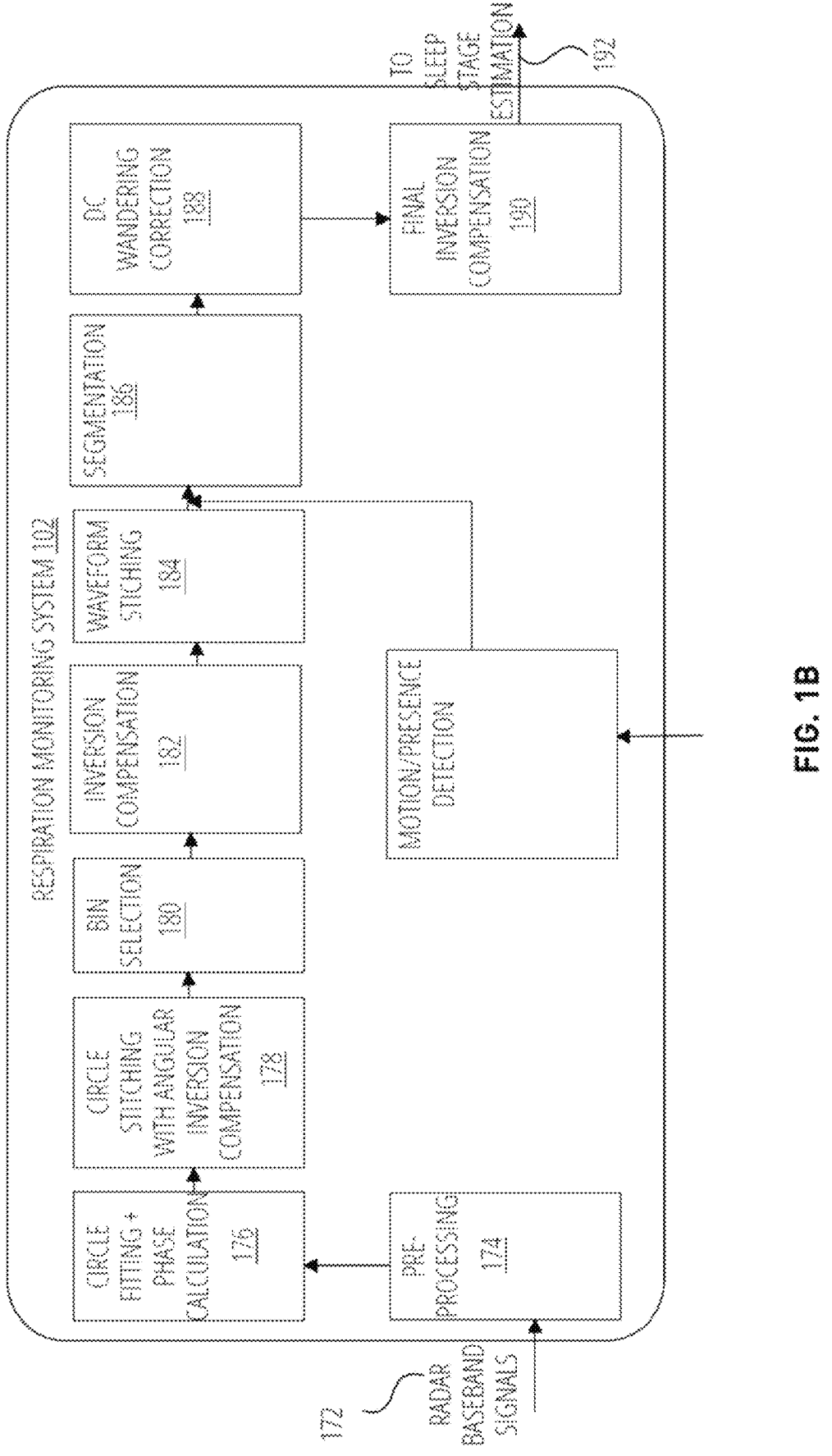
FIG. 1B is a flow diagram of a respiration monitoring system for generating a respiration waveform from radar baseband signals according to at least one embodiment.

FIG. 1B is a flow diagram of a respiration monitoring system 102 for generating a respiration waveform 192 from radar baseband signals 172 according to at least one embodiment. The respiration monitoring system 102 includes various functional blocks to perform signal processing on the radar baseband signals 172 to generate the respiration waveform 192 that is input into a sleep stage estimation ML model (not illustrated in FIG. 1B). The functional blocks represent digital signal processing blocks that are configured to perform the corresponding functions. The respiration monitoring system 102 can perform pre-processing operations on the radar baseband signals 172 in a first processing block 174. The respiration monitoring system 102 can perform circle fitting operations and phase calculations in a second processing block 176. The respiration monitoring system 102 can perform circle stitching with angular inversion compensation operation in a third processing block 178. Additional details of the circle fitting, phase calculations, circle stitching, and angular inversion compensation are described below with respect to FIGS. 4-5. The respiration monitoring system 102 can perform bin selection operations in a fourth processing block 180. Additional details of the bin selection operations are described below with respect to FIGS. 3-5, 14A. The respiration monitoring system 102 can perform inversion compensation operations in a fifth processing block 182. Additional details of the inversion compensation operations are described below with respect to FIGS. 7-8, FIG. 14B. The respiration monitoring system 102 can perform waveform stitching operations in a sixth processing block 184. Additional details of the stitching or combining operations are described below with respect to FIG. 4. The respiration monitoring system 102 can perform segmentation operations in a seventh processing block 186. Additional details of the segmentation operations are described below with respect to FIGS. 9-11. The respiration monitoring system 102 can perform DC wandering correction operations in an eighth processing block 188. Additional details of the DC wandering correction operations are described below with respect to FIGS. 12A-13. The respiration monitoring system 102 can perform final inversion compensation operations in a ninth processing block 190.

Additional details of the final inversion compensation operations are described below with respect to FIG. 7. It should be noted that, in other embodiments, the operations described in FIG. 1B can be performed in a different order. Also, some of the operations in FIG. 1B can be optional.

Figure 2:
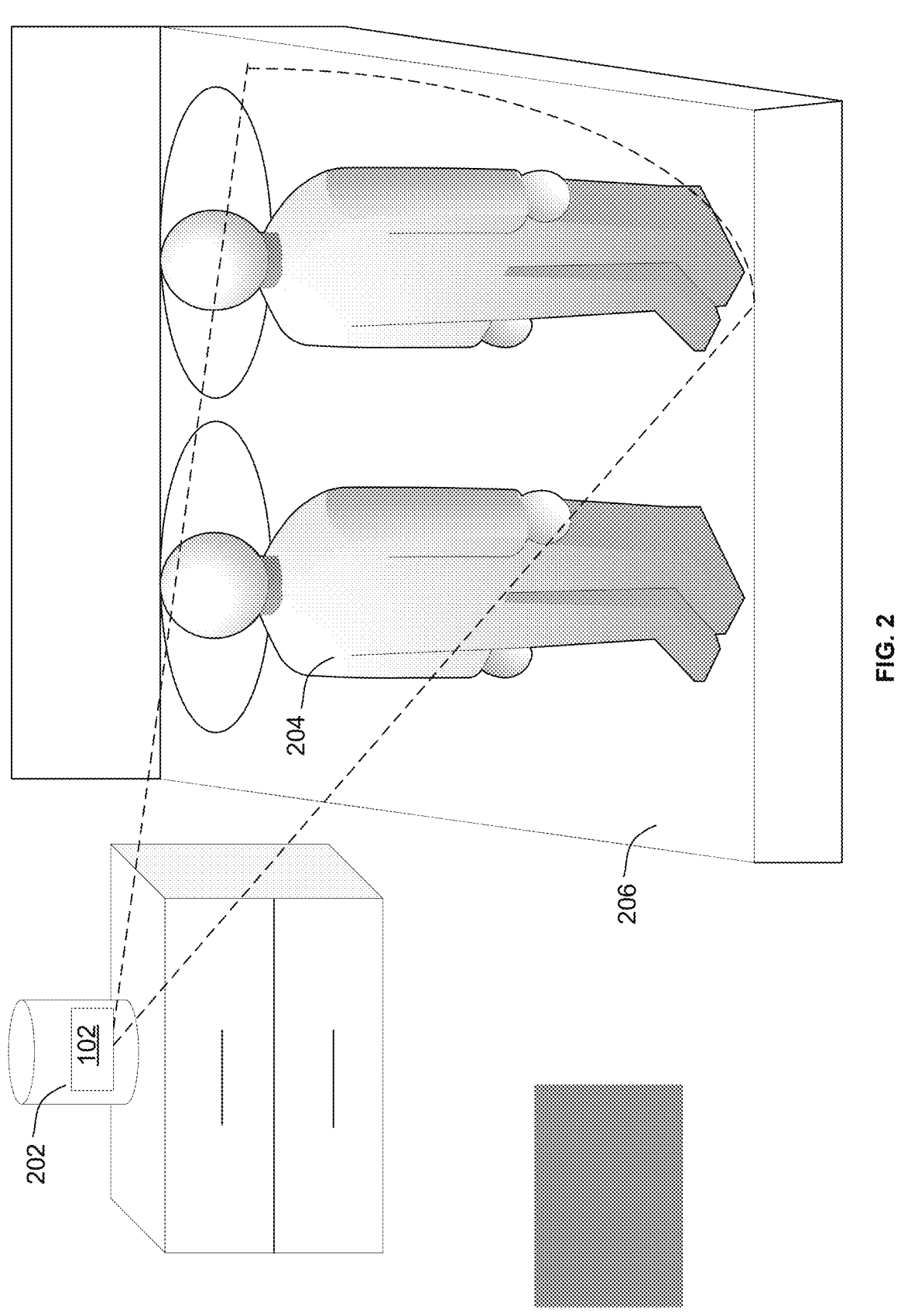
FIG. 2 illustrates a computing device including a respiration monitoring system for generating a respiration waveform from radar data for estimating a sleep stage of a human in a bed, according to at least one embodiment.

FIG. 2 illustrates a computing device 202 with the ML model 106 and the respiration monitoring system 102 for monitoring a sleep stage of a human 204 in a bed 206, according to at least one embodiment. The computing device 202 may include one or more radar units that monitor body motions, including tiny chest and abdomen movements during respiration. In this embodiment, the computing device 202 is connected to a router 208. In other embodiments, the computing device 202 can be located in other geographical regions and in connection with one or more APs. The computing device 202 may be able to detect, using the FMCW radar unit, the presence of a human 204 within an area of interest, which may be a three-dimensional area defined within a field of view of the FMCW radar unit. The area of interest may be manually defined or the computing device 202 may be able to generate and develop (e.g., expand or contract) the area of interest over a period of time by ignoring areas within the field of view that have little or no movement. The computing device 202 may determine, using the FMCW radar unit, that the human is in a first resting position. This may be performed, for example, by analyzing the signals generated by the radar unit. In one example, the signals generated by the radar unit may have a rhythmic waveform pattern (e.g., having periodic peaks and troughs), which may indicate a sleep stage of a user in the field view of the radar unit. The computing device 202 may receive a first waveform of the human resting in the first resting position, and a second waveform of the same human. The computing device 202 may determine that the first waveform has a higher signal-to-noise ratio (SNR) value than the second waveform, and therefore eliminate the second waveform from further analysis.

In at least one embodiment, the computing device 202 can estimate a sleep stage of a human in a contactless manner. The computing device 202 can include a housing, a processor, and a pulsed radar unit coupled to the processor. The processor can receive a first time series dataset associated with the human resting in a first position and a second time series dataset associated with the human resting in the first position. The processor can determine the first time series dataset has a higher signal-to-noise ratio value than the second time series dataset. The processor can determine that the first time series dataset has a first portion that has a first polarity and a second portion that has a second polarity. The processor can modify the second portion of the first time series dataset to have the first polarity. The processor can determine a phase shift between the first portion and the second portion. The first portion and second portion are consecutive portions in the first time series dataset. The processor can invert the second portion to compensate for the phase shift and combine the first portion with the second portion to form a third portion. The processor can determine a sleep stage of the human based on the shape of the third portion.

In a further embodiment, the processor can receive a third time series dataset from the pulsed radar sensor. The processor can determine a segment circle center in a first portion of the third time series dataset. The processor can offset the first portion from the segment circle center. The processor can detrend the first portion with a third order polynomial. The processor can detrend and apply a median filter to the first portion. The processor can determine the first portion satisfies a predefined criterion. The processor can invert a polarity of the first portion. The processor can determine the first portion satisfies the predefined criterion by correlating the first portion that is offset by the segment circle center with the first portion offset by a preceding segment circle center.

In a further embodiment, the processor can receive a fourth time series dataset and a fifth time series dataset from the pulsed radar unit. The fourth time series data set and the fifth time series dataset can be non-overlapping or partially overlapping. The processor can determine a correlation value between the fourth time series dataset and the fifth time series dataset using one of forward windowing, centered windowing, or backward windowing. The processor can invert the fifth time series dataset responsive to determining that the correlation value is less than a predetermined threshold. The processor can combine the fourth time series dataset and the fifth time series dataset to form a sixth time series dataset.

In a further embodiment, the processor can delete the seventh time series dataset and combine a segment immediately preceding the seventh time series dataset and a segment immediately succeeding the seventh time series dataset, responsive to determining that a motion-sensing metric, a presence-sensing metric, a respiration energy metric, or a coefficient of variation of radius of a seventh time series dataset is outside of a respective predetermined threshold range.

In a further embodiment, the processor can divide the combined time series dataset into a plurality of segments. The processor can determine a skewness value for each of the plurality of segments. The processor can invert the first segment responsive to determining that the skewness value of a first segment is greater than a predetermined threshold value.

In another embodiment, the computing device 202 includes at least one processor a radar unit communicatively coupled with the at least one processor, and a memory storing instructions that, when executed by the at least one processor, cause the computing device 202 to perform various operations as set for the below. The processor(s) can detect a presence of a human within an area of interest of the radar unit. The processor(s) can receive a first dataset indicative of the human resting in a first resting position. The processor(s) can receive a second dataset indicative of the human resting in the first resting position. The processor(s) can determine that the first dataset has a higher signal-to-noise ratio value than the second dataset. The processor(s) can determine that the first dataset includes a first portion that has a first polarity and a second portion that has a second polarity. The processor(s) can modify the second portion to have the first polarity to generate modified first dataset. The processor(s) can determine a sleep stage associated with the human based on a shape of the modified first dataset.

In a further embodiment, the processor(s) can determine a phase shift between the first portion and the second portion and compensate for the phase shift, wherein the first segment and second segment are consecutive segments. The processor(s) can combine the first portion with the second portion to form a combined first dataset.

In a further embodiment, the processor(s) can receive a third dataset and determine a segment circle center in a first segment of the third dataset. The processor(s) can offset the first segment from the segment circle center. The processor(s) can detrend the first segment with a third order polynomial. The processor(s) can detrend and apply a median filter to the first segment. The processor(s) can determine the first segment satisfies a predefined criterion. The processor(s) can invert the first segment.

In a further embodiment, the processor(s) can determine the first segment satisfies the predefined criterion by correlating the first segment that is offset by the segment circle center with the first segment offset by a preceding segment circle center to determine the first segment has to be inverted.

In a further embodiment, the processor(s) can determine a correlation value between a fourth dataset and a fifth dataset using one of forward windowing, centered windowing, or backward windowing. Responsive to determining that the correlation value is less than a predetermined threshold, the processor(s) can invert the fifth dataset. The processor(s) can combine the fourth dataset and the fifth dataset to form a combined dataset.

In a further embodiment, the processor(s) can divide the combined dataset into a plurality of segments. The processor(s) can determine a skewness value for each segment in the plurality of segments. The processor(s) can invert the first segment responsive to determining that the skewness value of a first segment is greater than a predetermined threshold value.

In a further embodiment, the processor(s) can delete the sixth dataset and combine segment immediately preceding the sixth dataset and immediately succeeding the sixth dataset, responsive to determining that a motion sensing metric, a presence sensing metric, a respiration energy metric, or a coefficient of variation of radius of a sixth dataset is outside of a respective predetermined threshold range.

In another embodiment, the computing device 202 can monitor the sleep stage of a human in a contactless manner. The computing device 202 can include a housing, a processor within the housing, and a radar unit within the housing and coupled to the processor. The processor is configured to detect, using the radar unit, presence of a human within an area of interest. The processor is configured to receive a first time series dataset associated with a first spatial region within the area of interest. The processor is configured to receive a second time series dataset associated with the first spatial region, wherein the first time series dataset immediately precedes the second time series dataset. The processor is configured to determine a first circle center offset for the first time series dataset and a second circle center offset for the second time series dataset. The processor is configured to apply the first circle center offset to the first time series dataset, convert to phase to form a first modified first time series dataset, and detrend the first modified first time series dataset. The processor is configured to apply the second circle center offset to the second time series dataset, convert to phase to form a first modified second time series dataset, and detrend the first modified second time series dataset. The processor is configured to apply the first circle center offset to the second time series dataset, convert to phase to form a second modified second time series dataset, and detrend the second modified second time series dataset. The processor is configured to determine a phase correlation between the first modified second time series dataset and second modified second time series dataset, and, responsive to the phase correlation satisfying a predefined criterion, invert the first modified second time series dataset. The processor is configured to combine the first modified first time series dataset and the inverted first modified second time series dataset to form a first combined time series dataset. The processor is configured to determine a sleep stage of the human based on the first combined time series dataset.

In a further embodiment, the processor is configured to receive, from the radar unit, a third time series dataset from the first spatial region within the area of interest. The second time series dataset immediately precedes the third time series dataset. The processor is configured to receive a fourth time series dataset from a second spatial region within the area of interest and over the same time period as the second time series dataset. The processor is configured to receive a fifth time series dataset from the second spatial region within the area of interest and immediately after the fourth time series dataset. The processor is configured to add the second time series dataset to the first time series dataset to form a second combined time series dataset to determine the sleep stage responsive to determining that the second time series dataset has higher metrics than the fourth time series dataset. The processor is configured to determine that the fifth time series dataset has higher metrics than third time series dataset. The processor is configured to determine a phase correlation between the second times series dataset and the fifth time series dataset. The processor is configured to modify a polarity of the fifth time series dataset to match a polarity of the second time series dataset. The processor is configured to add the modified fifth time series dataset to the second combined time series dataset.

In a further embodiment, the processor is configured to detrending the second combined time series dataset with a third-order polynomial. The processor is configured to detrend and apply a median filter to the second combined time series dataset. The processor is configured to apply forward windowing, center windowing, and backward windowing to the second combined time series dataset.

In a further embodiment, the metrics comprise two or more of a respiration energy metric, a coefficient of variation of circle radius from circle fit, signal to noise ratio, and a peak-to-peak statistic.

In a further embodiment, the processor is configured to apply a motion-sensing metric and a presence-sensing metric to divide the second combined time series dataset into a plurality of segments. The processor is configured to determine skewness value for each of the plurality of segments. Responsive to determining that a skewness value for a segment is larger than a threshold value, the processor is configured to invert the segment.

Figure 3:
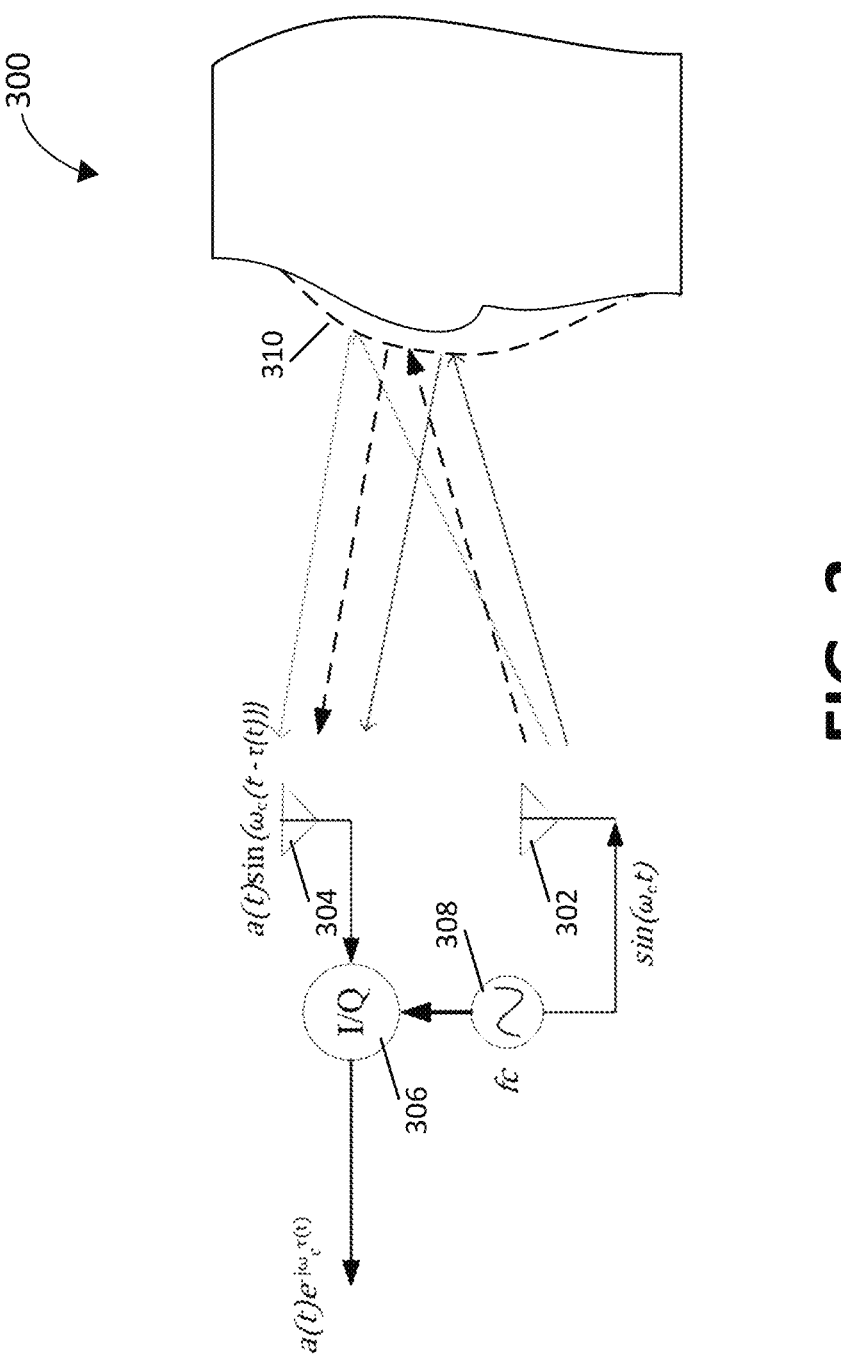
FIG. 3 illustrates functionality of a frequency-modulated continuous wave (FMCW) radar unit, according to at least one embodiment.

FIG. 3 illustrates an example radar-based computing device 300, according to one embodiment. The mmWave radar-based computing device 300 may include transmit (Tx) 302 and receive (Rx) 304 radio frequency (RF) components, one or more I/Q mixers 306, one or more synthesizers 308, analog components such as clocking circuits, and digital components such as analog-to-digital converters (ADCs), microcontrollers (MCUs) and digital signal processors (DSPs). The radar-based computing device 300 may also include metal-oxide-semiconductor (CMOS)-based mmWave radar devices that integrate TxRF and RxRF analog components such as clocking circuits, and digital components such as the ADC, MCU, and hardware accelerator. In one embodiment, the radar unit may include a FMCW radar unit. The FMCW radar may transmit a frequency-modulated signal continuously in order to measure range as well as angle and velocity. The human chest cavity 310 moves as a result of breathing and heartbeat. In one embodiment, the computing device 300 may include a 60 GHz FMCW radar unit with a 4 GHz bandwidth. Using the computing device 300, any two reflected paths from the chest with a roundtrip path difference exceeding ~4 cm can be resolved or measured independently. Since the radar measures displacement in a radial direction, a location with the strongest component of displacement in the radial direction is the best location to measure breathing. It should be noted that radial motion can be sufficient, but the best angle may not be obtained to get the maximum radial motion. People change their sleep position throughout the night tens of times, and accordingly, the best location to observe breathing also changes. "Binning" is a mechanism to select the best location (such as a range bin) to observe breathing waveform. If the best bin is not chosen, the selected breathing waveform has low fidelity (when compared with the ground truth). This impacts the quality of the waveform features adversely and can degrade the subsequent sleep stage estimation by the ML model. In case of double occupancy, binning also needs to ensure that it tracks the breathing of an intended user (e.g., the user closest to the radar unit), and does not accidentally lock onto an unintended user. An unintended user is a user that is detected in the field of view, but is not the intended user for whom sleep stages are being estimated.

An operational mode is a mode of operation of the radar unit that defines particular parameters and functionality that impact the complexity of sensing operations and thus power consumption as well. For example, an operational mode may selectively activate certain hardware within the radar unit. Further, an operational mode may selectively activate certain firmware (or software) processes running in that operational mode. As more hardware, sensing resources, and processing power are employed in a higher operational mode, more power is likewise consumed, as will be explained in detail.

Because the monitored area of the computing device for most residences and even businesses remains uninteresting most of the time, a first operational mode may be an idle mode that consumes very little power. If no motion is detected in an area of interest, which may be a three-dimensional area defined within a field of view of the radar unit, then the processor may continue to operate the radar unit in the first operational mode. Thus, the first operational mode may be the most frequently active mode (in comparison to other modes described below), and may further operate at the lowest power compared to other modes.

According to some embodiments, while operating in the idle mode, the radar unit may be configured with the minimum operational complexity needed in order to make a binary decision, for example, whether or not there is some kind of motion present. Because the idle mode does not have much complexity, the radar unit may not completely localize the origin of the motion or distinguish between a human-like motion or another type of motion, for example, curtains swaying. While operating in the idle mode, the radar unit preferably has a zero false-negative rate, but some false-positives are acceptable, where a false-negative occurs when motion is present within the security perimeter, but the radar unit fails to detect the motion, and a false-positive occurs when no motion is present within the security perimeter, but the radar unit detects motion. In the idle mode, the radar unit is capable of ranging moving objects and can be configured to set a radial security perimeter, which, when breached (or has motion occurring inside), causes the processor to trigger the radar unit to transition from the first operational mode to a second operational mode, also referred to herein as an observational mode.

In a FMCW radar unit, a transmitted signal of a known stable frequency continuous wave varies up and down in frequency over a fixed period of time by a modulating signal. The frequency difference between the receive signal and the transmit signal increases with delay, and hence with distance. This process mixes or demodulates the Doppler signal. Reflections (or echoes) received back from a target are then mixed with the transmitted signal to produce a beat signal, which gives the distance of the target after demodulation. Typically, a FMCW radar possesses range information, which is beneficial to separate multiple targets and isolate the surrounding clutter in the scenario. Moreover, using phase-based radar interferometry technique, FMCW radar can achieve excellent capacity to measure small displacement variation. However, reflections from the stationary object (i.e., static clutter) nearby the desired target can interfere with the wanted signals backscattered from the moving scatterers in the same range bin, and thus cause the estimated displacement time series are smaller than the truth. Sometimes, it may be difficult to isolate the clutter component from the original beat signal, because they are mixed in the time domain and their frequencies are very similar. While uses of the term vary in the art, "chirps" herein refer to a cycle of a radar signal that changes in frequency throughout a period of time before repeating.

Furthermore, a frame may be understood to be a period of time during which the radar unit samples the monitored area with the transmit signal, which includes the chirps, to capture a dataset capable of being processed by one or more processing functions to perform object detection. As such, each frame may include multiple chirps in order to capture sufficient data for object detection processing, although a single chirp is sufficient for mere motion detection. A chirp sent out reflects off surfaces and returns to the radar unit as reflection signals.

A pulse radar is a radar system that employs a repetitive series of short-duration pulses that make up a larger frame. Each larger pulse may thus define a pulse width or a pulse duration. A pulse repetition period, e.g., the period between each large pulse, may define a pulse rate, e.g., the number of the large pulses per second. The reflected radar signals, from the transmitted radar pulses, may be processed in order to determine distance. The range accuracy of a pulse radar depends on the width of the pulse: the shorter the pulse, the better the accuracy. Short pulses, however, require wide bandwidths in the receiver and transmitter (since bandwidth is equal to the reciprocal of the pulse width). The bandwidth (BW) is the difference between the upper and lower cut-off frequencies of the transmitter and receiver, and is usually measured in hertz (Hz). Because a pulse radar does not radiate continually, the average power is much less than the peak power. The average power, rather than the peak power, is the measure of the capability of a pulse radar system. Radar systems have average powers from a few milliwatts (mW) to as much as one or more megawatts (MW), depending on the application. A pulse radar consumes more power at a higher bandwidth, thus lower pulse width, and at higher frequencies, thus higher pulse rate.

A region of interest may further be defined as an area of interest to monitor human activity such as breathing. This region of interest may also be user programmable, and may cover a portion of the monitored area. While in the observational mode, the radar unit may better localize the source of motion and determine whether the activity detected by the idle mode was a false-positive, e.g., a motion outside of the region of interest. Better localization may be achieved by using two receive antennas, and by the radar unit using angle of arrival (AoA) estimation to determine a direction with reference to the radar unit from which the motion is being detected.

Figure 4A:
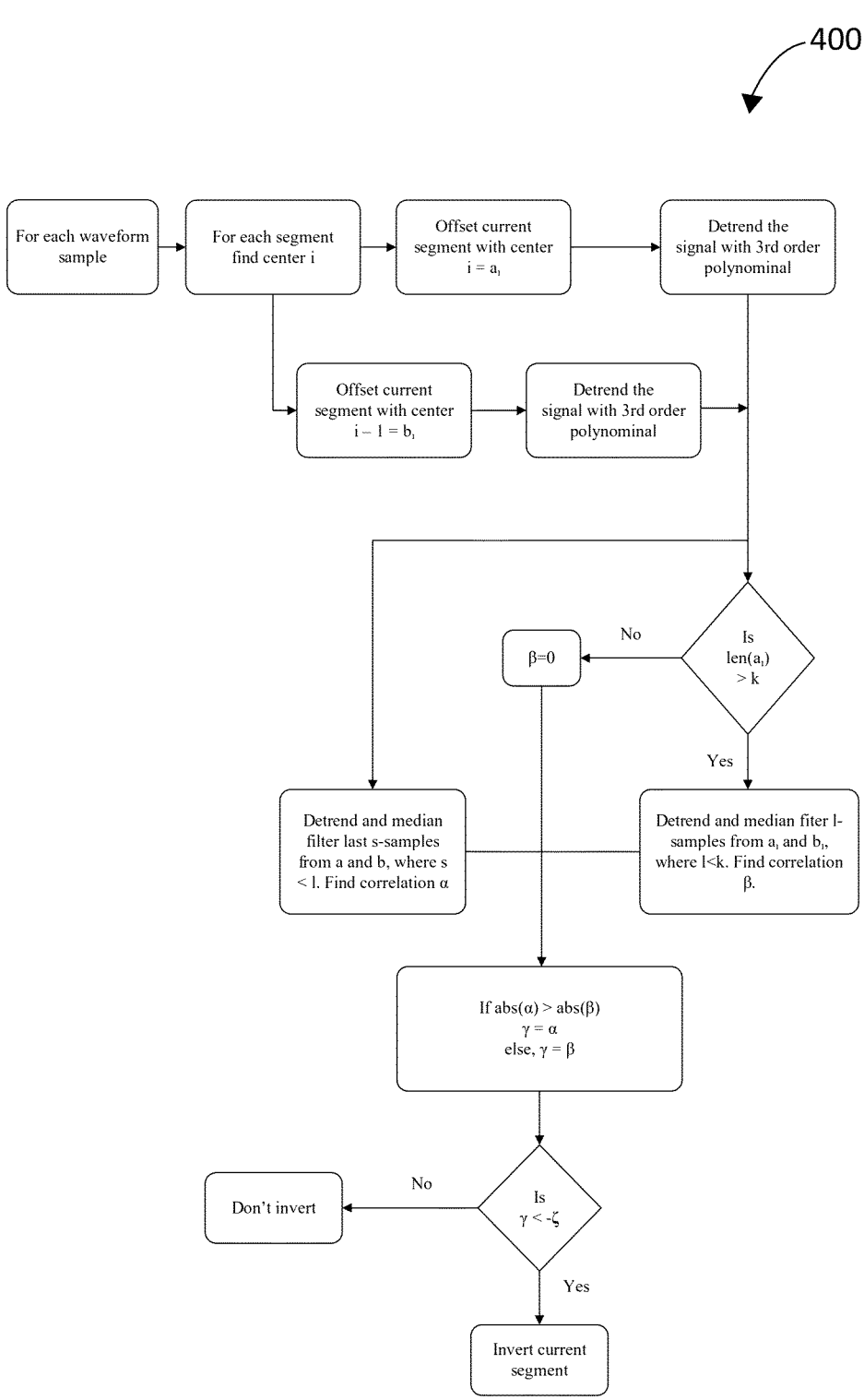
FIG. 4A is a flowchart of a method for performing angular inversion compensation in a radar-based computing device, according to at least one embodiment.

FIG. 4A illustrates a flowchart of a method 400 for operating a radar-based computing device in an embodiment. The method 400 may be performed by processing logic that may include hardware (circuitry, dedicated logic, etc.), software (such as is run on a general-purpose computer system or a dedicated machine), firmware, or some combination thereof. For example, the method 400 may be performed by the computing device 104, 202, and 1200 (illustrated and explained in further detail in FIG. 15 and FIG. 16), and particularly by the processor 1262 executing instructions stored in the memory 1340 for performance of aspects of the method 400.

The ML model 106 may require consistent waveform polarity (inhale and exhale) to predict sleep stages accurately. Therefore, it is important to have the radar waveform with correct polarity over time in all the bins and one of the main reasons for inconsistent waveform is the small arc length during circle fitting, which may get even worse with noise. In the presence of clustered outliers, both for complete and incomplete arcs, the fitted circles may be biased to outliers because of the least squares error distance criterion, thereby improperly representing both the size (radius) of the circle and its position. This involves implementing circle fitting for the phasor representation which consists of a cloud of discrete points in the complex plane. Note that the actual phasor amplitude regarding the desired component can be considered constant because the intensity of reflected radar echoes is changeless owing to relatively small displacement variation for vibration and deflection monitoring. Moreover, the phasor amplitude may be inconstant for large-scale displacement tracking, and can also adopt signal segmentation along time to deal with this problem. Therefore, methods such as linear least squares fitting algorithm can be employed to perform the circle fitting, which results in the phasor offset (i.e., coordinate (x, y). The reason for this shorter arc length is the small radial displacement towards the radar that can be caused by different body positions or movements while facing the radar.

Accordingly, in one embodiment, a post-processing procedure based on phasor offset compensation (POC) can be used to eliminate the static clutter interference, which can be implemented by using an updated signal processing algorithm and achieve accurate displacement measurement. Least square method or least square regression is one example method for curve fitting, where the best-fit curve/line corresponding to a set of data points can be obtained. This approach minimizes the sum of the square of the errors (or residuals) in the set of data points. Other example methods for circle fitting include using Hough transform and the Taubin method.

In addition to circle fitting, which is performed in phasor domain and does not use time-based features to improve fitting, additional signal processing can be performed, such as de-trending trends in the data. Any time series dataset may contain a trend, which is a continued increase or decrease in the time series over time. There can be benefits in identifying, modeling, and removing trend information from a time series dataset. In general, a systematic change in a time series that does not appear to be periodic is known as a trend.

Accordingly, one method involves signal conditioning with median filtering and third-order detrending. An identified trend can be modeled, and it can be removed from the time series dataset. This is called "detrending" the time series. If a dataset does not have a trend or the trend has been removed, then the dataset is said to be trend stationary. The method may also include a correlation of the current signal that is offset by a current circle center of the point cloud data with the same signal but offset by the previous segment circle center of the point cloud data to determine if the current segment needs to be inverted or not. A circle center is the result of the circle fitting operation and represents the center of the circle. The current circle center is from a first dataset at a first time and the previous segment circle center is from a second dataset at a second time before the first time. The method may further include phase shift compensation between consecutive segments for final waveform "stitching" or combining. The phase shift compensation step may include compensating (e.g., increasing or decreasing) the phase values according to a phase shift observed between a first segment and a second segment. An example of a phase shift is illustrated in FIG. 5 around point 3000.

First, for each bin of the radar signal, the current segment is offset with the circle center: i, or ai, and the current segment is offset with the previous circle center: i-1, or $b_i$. FIG. 4B illustrates a first graph 402 with the current segment 404 offset from a previous circle center 406 and a second graph 408 with the current segment 410 offset from a current circle center 412, according to at least one embodiment. Next, the radar data (e.g., point cloud data) is smoothed with median filtering and then detrend the radar data with a third-order polynomial. If the length of the current segment is greater than k, which is a predetermined constant length, then the processing logic would detrend and apply a median filter to I-samples from the current segment. The method further includes finding a first correlation coefficient β. If the length of the current segment is less than k, the processing logic would detrend and median filter to s-samples from the current and delayed segment. At this point, the processing logic next finds a second correlation coefficient α. If the abs(α) is greater than abs(β), then the final coefficient of correlation γ is determined to be β, else γ=α. Once final coefficient of correlation γ is determined, the processing logic checks against a predefined threshold of, −ζ. If γ<ζ, then the processing logic inverts the current segment. Next, the processing logic compensates for any phase shift between two consecutive segments in a bin before stitching/combining the waveform for that bin.

Figure 5:
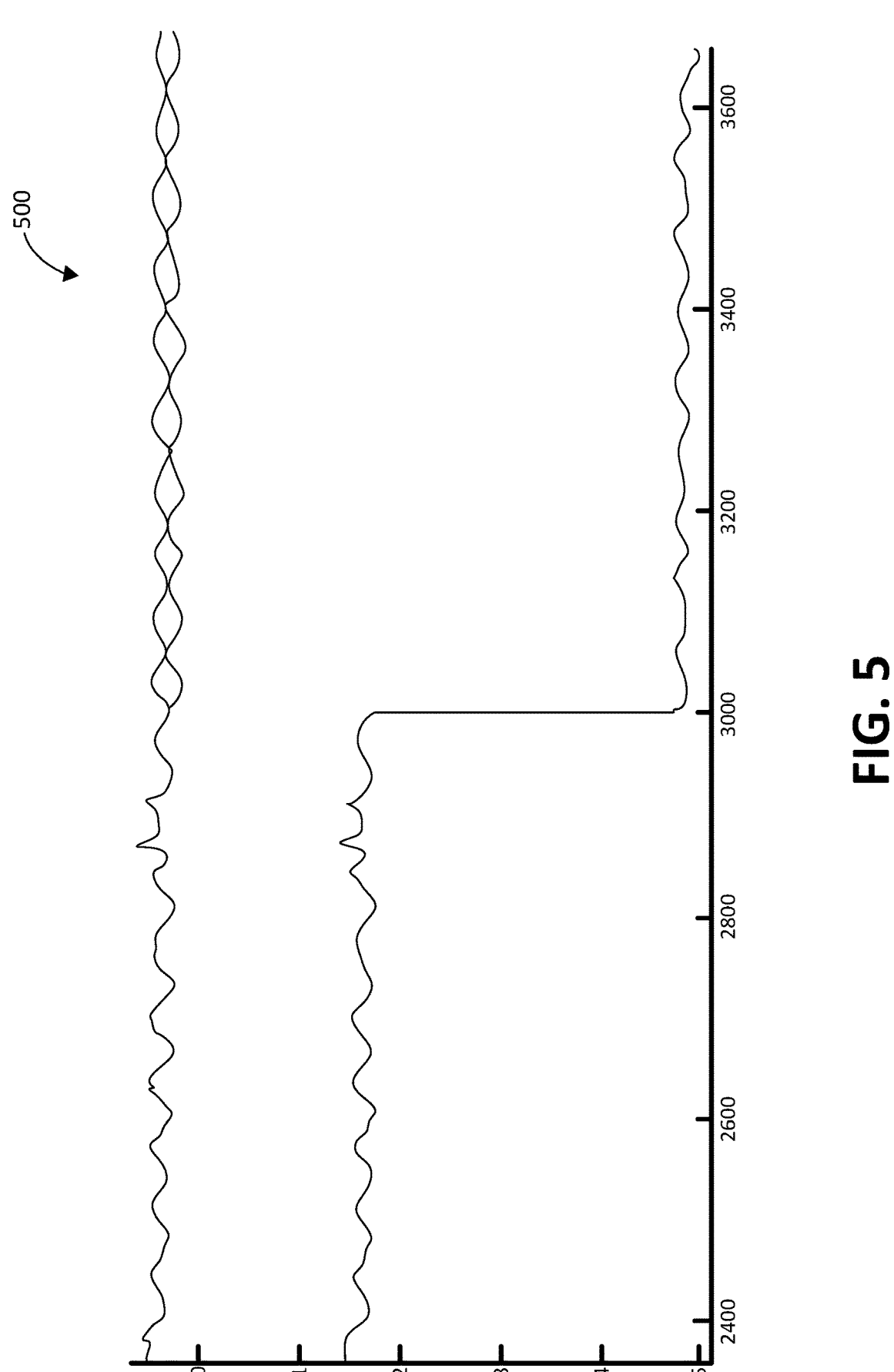
FIG. 5 is a sample graph illustrating angular inversion compensation performed by a radar-based computing device, according to at least one embodiment.

FIG. 5 illustrates a temporal waveform 500 shown before and after angular compensation explained with respect to FIG. 4. It can be observed here that the angular inversion and phase shift at point 3000 on the dark line in the plot. The lighter line shows the stitching/combining at 3000 but has angular inversion present at point 3000.

In one embodiment, the radar-based computing device uses a respiration energy metric (e.g., signal-to-noise ratio (SNR)) as one of the metrics. This frequency-based metric is a ratio of the energy in the breathing frequency range over the energy outside of the breathing frequency range. The waveform also contains energy attributable to wandering direct current (DC) or baseline wander, which is unrelated to breathing. DC wandering or baseline wandering is a phenomenon noticed in signal processing where a filter's own frequency response can create an underlying pattern. The filters can cause the middle of the data (e.g., point cloud data) eye to wander with low-frequency components in the data stream. This unwanted DC wandering may be removed from the breathing waveform iteratively to improve the sensitivity of estimating respiration energy. Similarly, since respiration can have a wide range of frequencies (i.e., periodicity) from person to person, using a single frequency interval to determine respiration energy results in desensitization due to noise. Hence, multiple frequency intervals are considered such that each interval includes the fundamental and higher harmonics of respiration to maximize the respiration energy while keeping the noise energy low.

Gating may be applied in one of the following ways: (a) Peak-to-peak: This is a time domain phase-based metric. A longer circle-arc in the phasor domain indicates a large displacement in the radial direction. A short arc indicates a smaller radial component. This could be due to a smaller chest displacement or an unfavorable angle of view. Similarly, an unusually large circle may be due to a large phase excursion caused by noise. These outliers are rejected via peak-to-peak gating. (b) Coefficient of Variation of Radius: This metric is based on the I/Q (phasor) domain. A large radius indicates a strong reflection from the chest. Typically, the reflectivity does not change frequently. Therefore, a coefficient of variation in the circle radius indicates a problematic bin. Hence, the bins with a larger coefficient of variation (i.e., the ratio of the standard deviation to the mean) for the radius are rejected via circle-radius gating. (c) Glitch: This is a metric based on a phase shift in the time domain. An incorrect estimate of the circle (both center and radius) or excessive noise may cause the arc of the circle crossing near the origin. These zero-crossings result in abrupt phase shifts (called "glitches"). For example, an I/Q point shifts from the second quadrant to the fourth quadrant. Breathing waveforms with excessive glitches indicate poor quality of waveform/circle-fitting and are rejected using glitch gating.

Based on the above metrics, the computing device may choose the best bin based on the metric as well as the prior selected bin. If the previous preferred bin is no longer one of the preferred bins currently, one of the bins closest to the previous best bin is likely to be the current best bin. An abrupt bin change only happens when sleep posture changes. In this case, first, the search is restricted to the nearby bins. If a good bin is not found, the bin search range is extended just enough to include an alternate measurement point for the same user. This procedure avoids extending the search range aggressively, and accidentally locking/tracking the breathing of an unintended user in case of dual occupancy on the bed.

Figure 6:
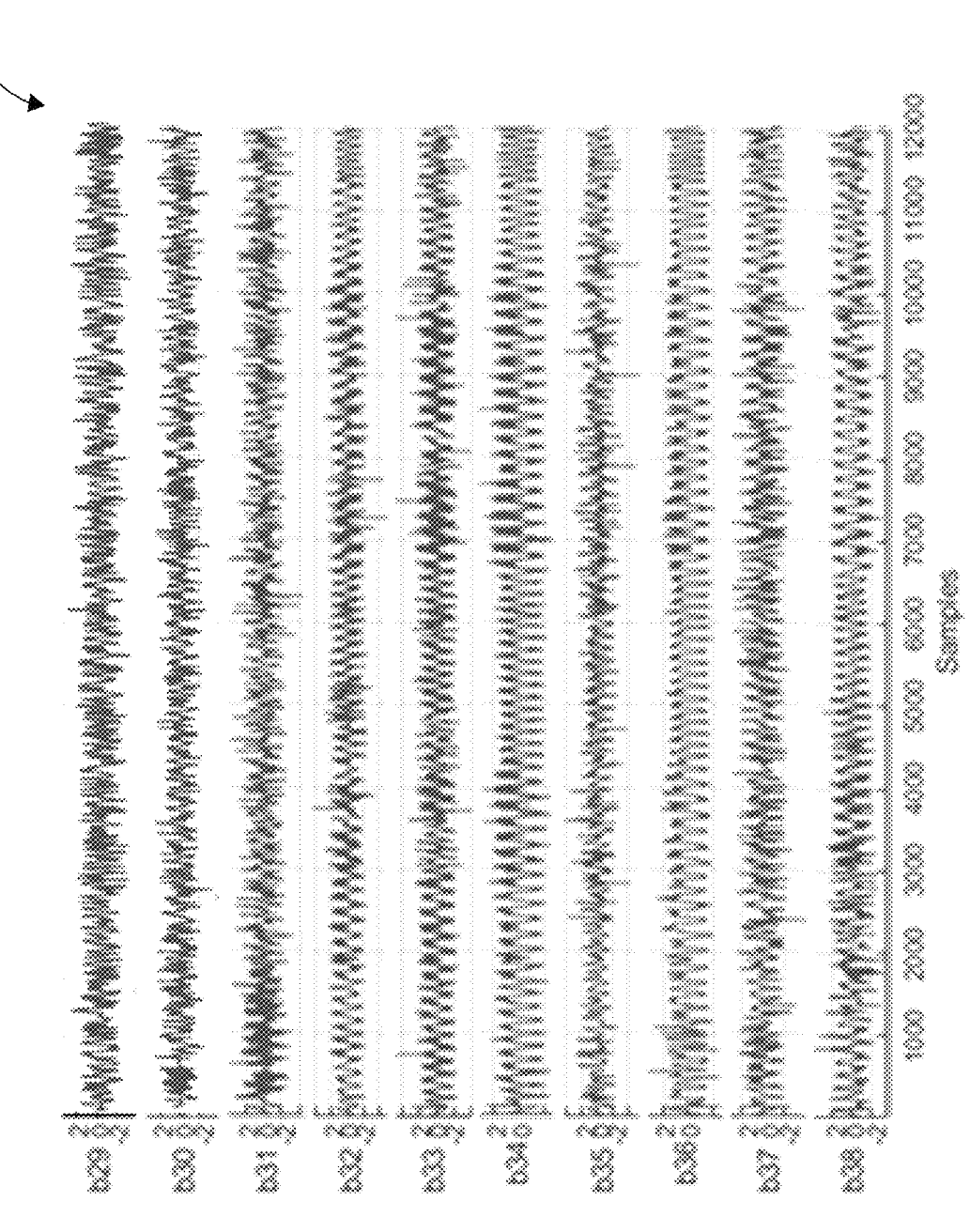
FIG. 6 is a sample graph illustrating waveform bin selection performed by a radar-based computing device, according to at least one embodiment.

FIG. 6 illustrates an example graph 600 with multiple bins b29-b38. Because bin b34 has a higher signal-to-noise ratio than bin b36, the computing device may use the waveform from bin b34 to process the signals further. However, the direction or the way a person faces a radar determines the radial component of the reflected electromagnetic (EM) wave for the radar. This characteristic is found in the radar signal if the subject moves or rolls (bin transition). The radar signal waveform after and before the bin transition can be either in the same polarity (in-phase) or inverse polarity (out of phase). Having the right waveform shape may be important if the radar signal is used for sleep stage estimation, and such polarity changes can affect the ML model.

Figure 7:
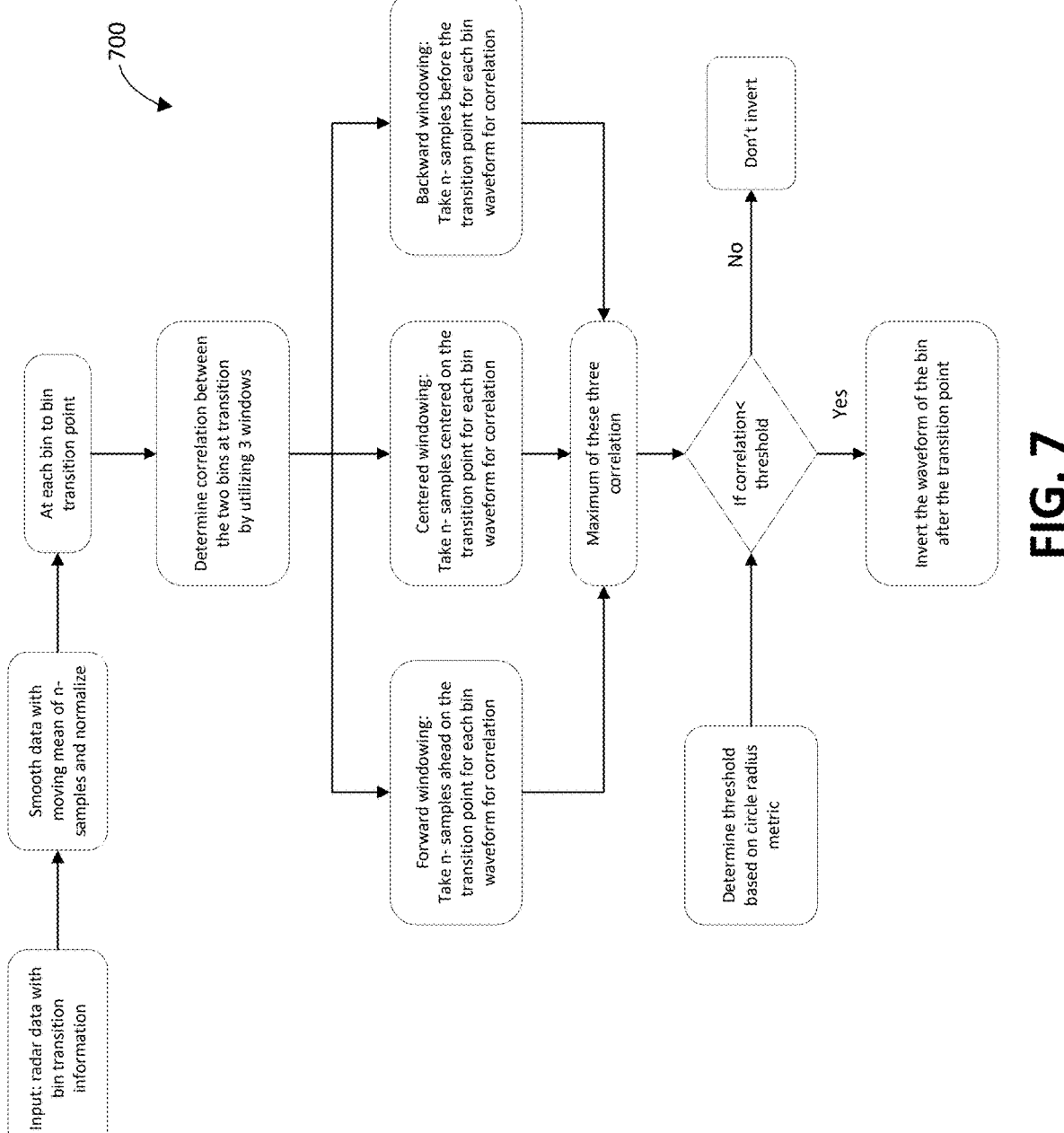
FIG. 7 is a flowchart of a method for performing inversion compensation by a radar-based computing device, according to at least one embodiment.

FIG. 7 illustrates a flowchart of a method 700 for operating a radar-based computing device in an embodiment. The method 700 may include inversion detection and compensation when there is a bin-to-bin transition, and final inversion correction and compensation with a statistical metric of skewness for all valid segments. The inversion detection and compensation for radar data can be divided into two parts: (1) radar bin-to-bin inversion detection and compensation, and (2) overall radar signal waveform inversion detection and compensation for each valid segment. In the first part, radar data with the bin transition information is smoothed out with a moving mean filter of n-samples and then normalized.

At each bin-to-bin transition, the correlation of radar waveform from the previous bin to the next bin is performed in three different ways: (1) Forward windowing: correlating two waveforms at the transition point by taking forward n-samples and finding the forward correlation coefficient, $\alpha_1$. In the forward windowing/moving average method the smoothed value is the average of present n-samples and all subsequent n-samples within a time window. (2) Backward windowing: correlating two waveforms at the transition point by taking back n-samples at the transition point and determining the backward correlation coefficient, $\alpha_2$. In the backward windowing/moving average method each sample is smoothed by taking the average of the value and all previous values within the time window. An advantage of this method is that it can be immediately performed on streaming data (e.g., as a new value is recorded, it can be immediately smoothed using previous data in the same time series). (3) Centered windowing: correlating two waveforms at the transition point by taking n-samples centered at the transition point and determining the centered correlation coefficient, $\alpha_3$. In the centered windowing/moving average method each value is smoothed by averaging within the time window, where the value being smoothed is at the center of the window. For this method, the time window is split so that half of the window is used before the time of the value being smoothed, and half of the window is used after. All windows are smoothened. These correlations may be done with the same time axis. These time series data smoothing tools smooth a numeric variable of one or more time series data using forward, backward, and centered moving averages, as well as an adaptive method based on local linear regression.

Figures 8A, 8B:
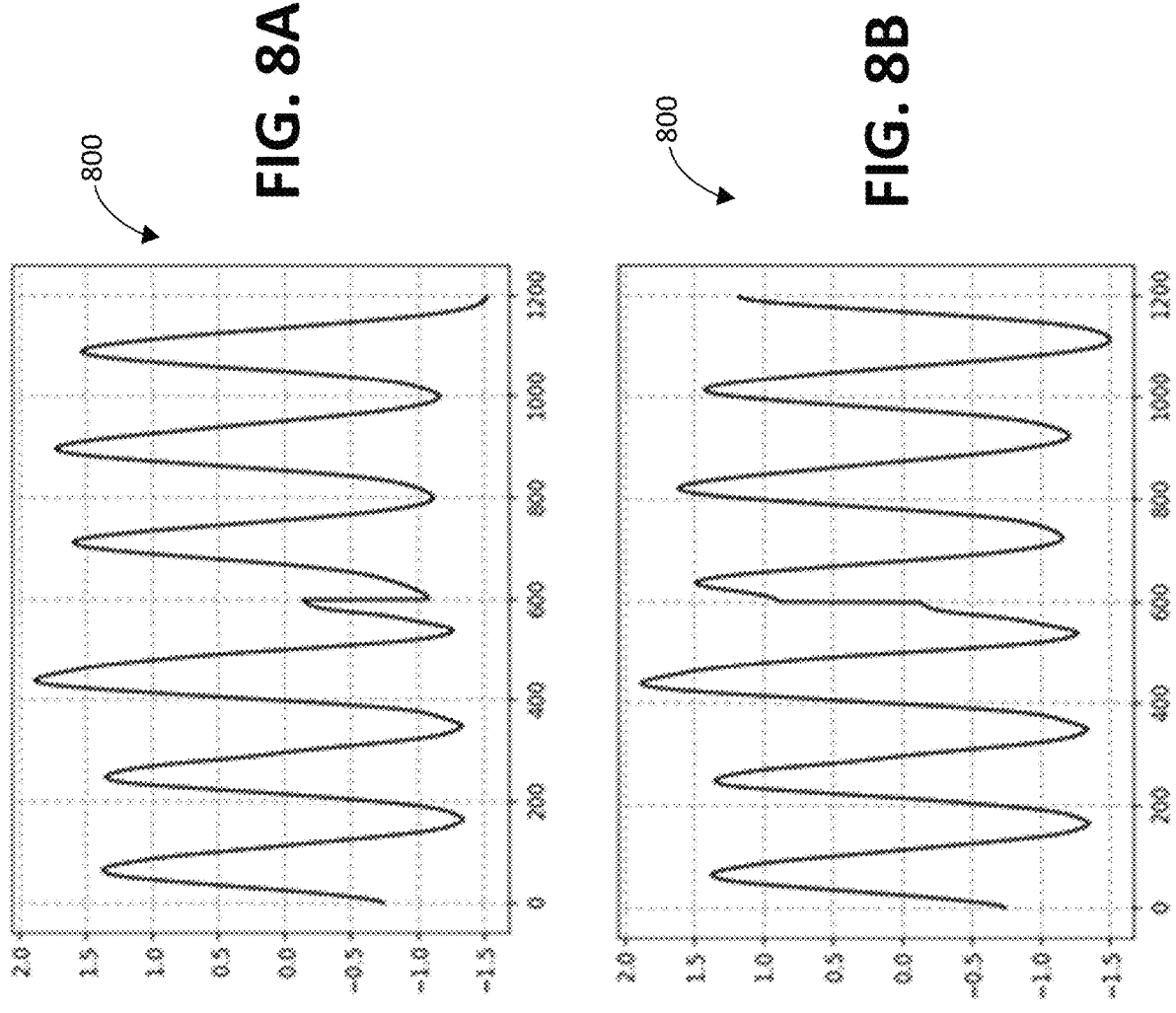
FIGS. 8A and 8B show sample graphs illustrating inversion compensation performed by a radar-based computing device, according to at least one embodiment.

After determining the three correlation coefficients, the processing logic may find $\beta$=max ($\alpha_1$, $\alpha_2$, $\alpha_3$). The processing logic may further determine the correlation threshold based on the circle radius metric and check if $\beta$ is less than that threshold. If $\beta$ is less than the correlation threshold, inversion is detected, and the waveform of the second bin is inverted with reference to the first bin. These steps can be propagated along all the bin transitions, and if these conditions are not met, then the waveform between the two bins is retained as is. After the inversion from bin-to-bin is corrected, the processing logic next checks the inversion for each valid segment. This is accomplished by using skewness as a metric. The right polarity waveform should have positive skewness for a normal breathing pattern, and the threshold is kept at $\zeta$. FIG. 8A illustrates a sample waveform 800 without inversion compensation, and FIG. 8B illustrates the same waveform with inversion compensation.

Figure 9:
FIG. 9 is a flowchart of a method for performing segmentation in a radar-based computing device, according to at least one embodiment.

FIG. 9 illustrates a flowchart of a method 900 for operating a radar-based computing device in an embodiment. For the ML model to predict sleep stages accurately, it may be important that noisy data or invalid data be filtered out from the overall radar data. It may also be important that the signal conditioning operations need to be performed only on valid segments so that DC wandering and per-segment inversion logic do not fail. Accordingly, the radar data is said to be invalid if there is no person in the radar's area of interest, there is motion causing the radar data to be irregular, or most of the data in a segment is invalid. In order to take care of such segmentation of radar data, the method 900 may include a motion and motion scene threshold, which is determined with a time averaging window on the motion and presence signals. This threshold is then used to flag invalid data. The method may also use the respiration energy metric (e.g., signal-to-noise ratio) in conjunction with a coefficient of variation of radius (i.e., the ratio of standard deviation to the mean) to derive a threshold that marks invalid data. For example, a large radius indicates a strong reflection from the chest. Typically, the reflectivity does not change frequently. Therefore, a coefficient of variation in the circle radius indicates a problematic bin. Hence, bins with a larger coefficient of variation (i.e., the ratio of standard deviation to the mean) for the radius are rejected via circle-radius gating. The method may also append all frames in a segment and check if the length of the short valid segments is less than a set threshold. If yes, then the processing logic marks that short segment as invalid.

As shown in FIG. 9, for each frame, the processing logic determines motion threshold, $\alpha$, and motion-scene threshold, $\beta$, and presence threshold, $\gamma$, from the PUT algorithm and respiration energy metric, $\zeta$ (e.g., signal-to-noise ratio), and coefficient of variation of radius, $\eta$. For example, a large radius indicates a strong reflection from the chest. Typically, the reflectivity does not change frequently. Therefore, a coefficient of variation in the circle radius indicates a problematic bin. Hence, bins with a larger coefficient of variation (i.e., the ratio of standard deviation to the mean) for the radius are rejected via circle-radius gating. Next, the processing logic checks if any of the following conditions are met: Motion near selected bin>=$\alpha$, Presence<=$\beta$, Motion scene>$\gamma$, $\zeta$=0 or $\eta$<=1: absence, or $\omega$>=529, where $\omega$=f ($\zeta$, $\eta$): function of the thresholds. If any of these conditions are met, then the processing logic flags that frame as invalid in that segment. Next, the processing logic checks for the short segment if the number of valid frames is less than a given threshold of $\mu$, if yes, the processing logic marks that short segment as invalid.

Figure 10:
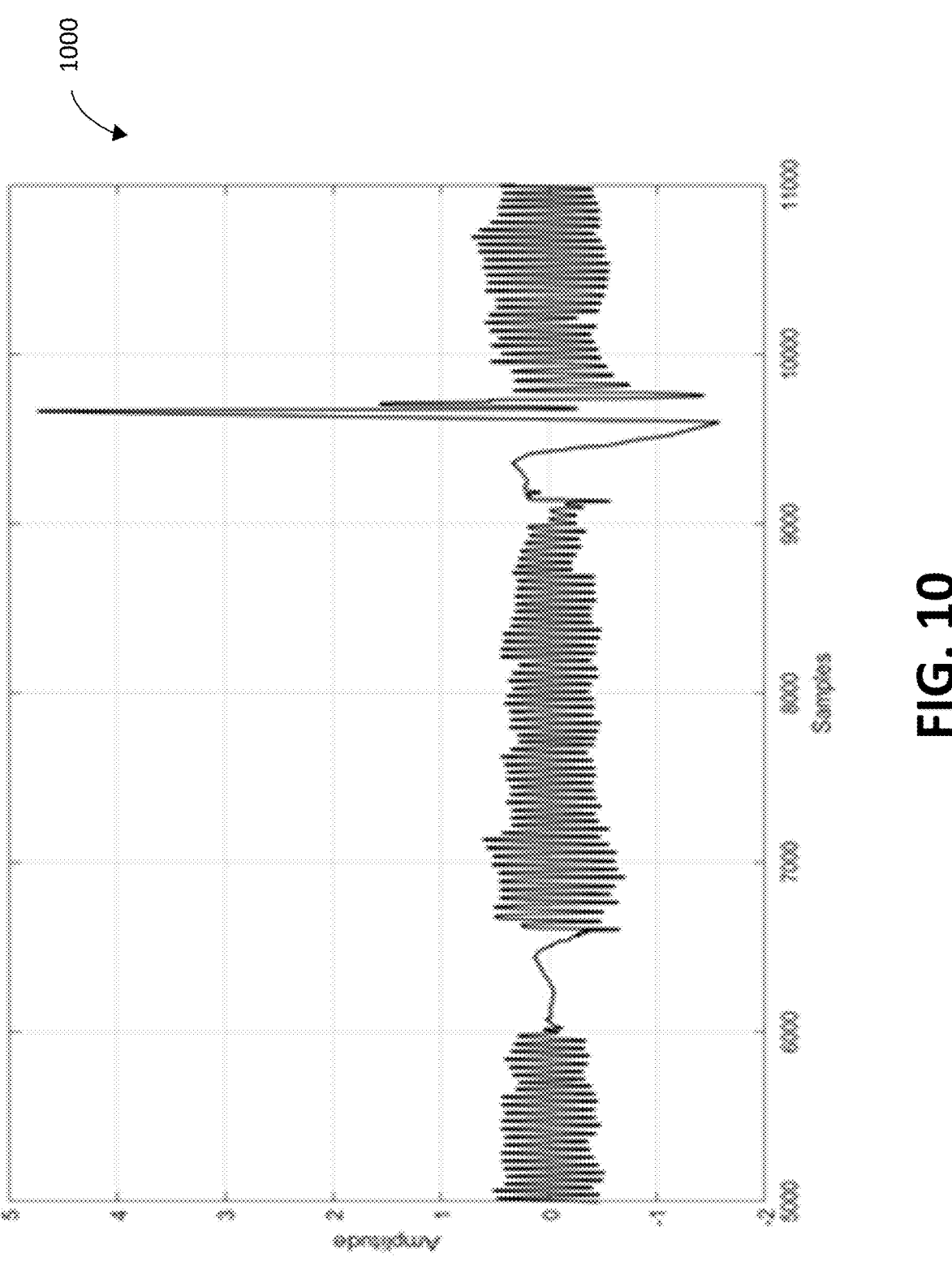
FIG. 10 is a sample graph illustrating a respiration waveform prior to segmentation performed by a radar-based computing device, according to at least one embodiment.
Figure 11:
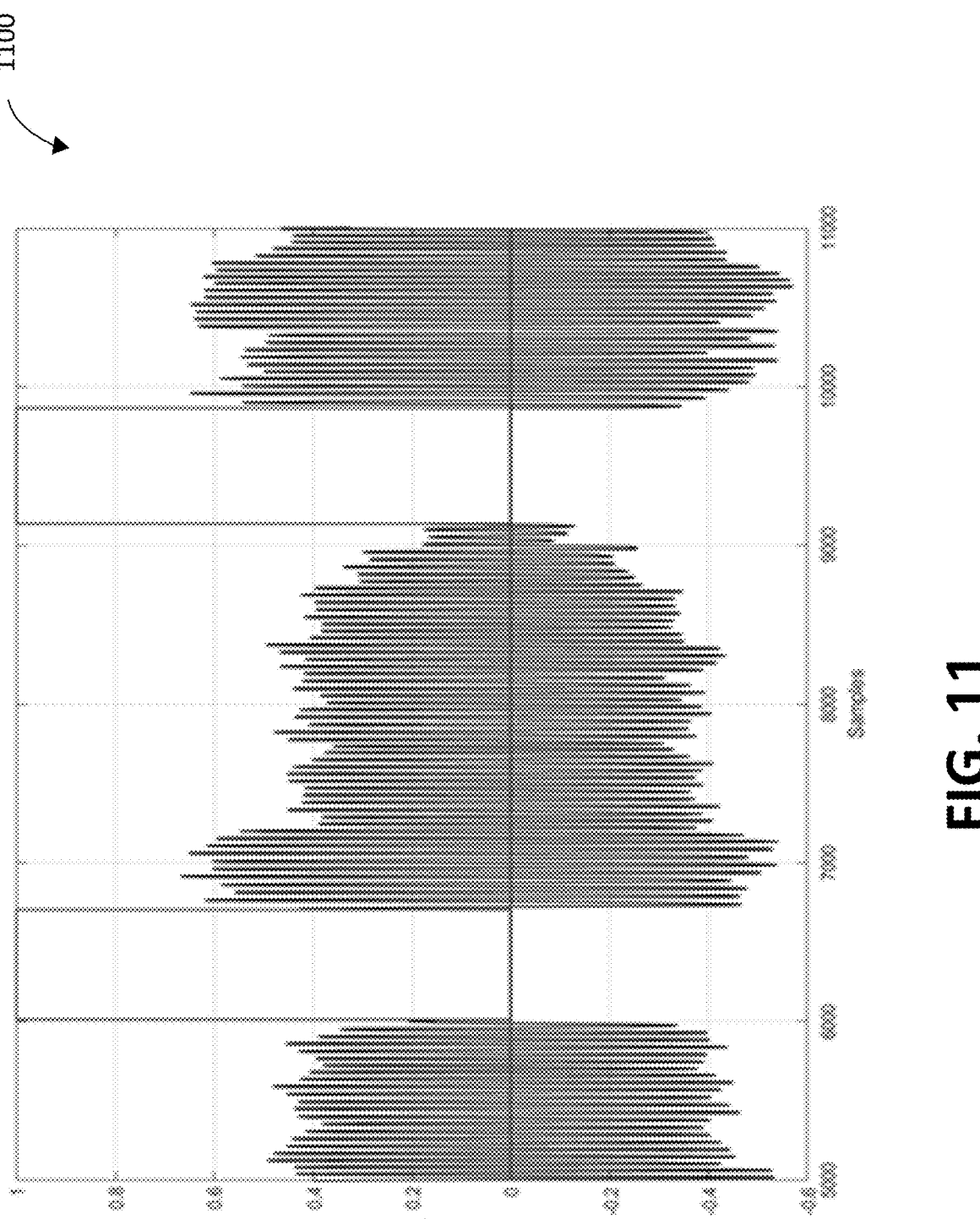
FIG. 11 is a sample graph illustrating a respiration waveform after performing segmentation by a radar-based computing device, according to at least one embodiment.

FIG. 10 illustrates an example waveform 1000 before segmentation where the segment between ~6000-7000 and ~9000-10000 is an invalid segment. It should be noted here that there is no valid signal around frame 9000 and frame 10000, which can be overcome by the method described in FIG. 9. As illustrated in FIG. 11, during segmentation, the segment between ~6000-7000 and ~9000-10000 are marked as invalid, and there is no longer DC wandering around frame 9000 and frame 10000, resulting in a smoother waveform 1100.

Breathing waveforms can, however, contain an underlying trend (i.e., wandering DC) unrelated to breathing. This trend, if not corrected, can result in both increased mean square error between the estimated waveform and real data, and inaccurate estimates of breathing rate. This can be problematic when the waveforms of different physical units are normalized before comparison. Both breathing rates and unwanted trends have periodicities that can change over time.

In some embodiments, breathing waveform can be recovered by estimating and correcting for any wandering DC. Specifically, based on the estimated breathing rate, the most aggressive detrending can be used without distorting the signal of interest while minimizing any residual wandering DC. A typical breathing signal has a periodicity of 10-30 breaths-per-minute and could be between 5 and 45 BPM. It also contains a slow-varying trend slower than a breathing waveform in a given interval. Since the frequency of the breathing signal and the underlying trend change from one interval to another, dynamic filtering is required to ensure that the most aggressive detrending is performed without distorting the signal of interest. Since the underlying trend and respiration can change fairly quickly, time-based frequency estimation, such as peak counting, is used over a short interval. Additional constraints, such as the prominence of peaks, minimum separation between peaks, and minimum peak width, are used to avoid detecting any spurious peaks. This step can be used to estimate the frequency (beats per minute (BPM)) of the breathing signal.

Figures 12A, 12B:
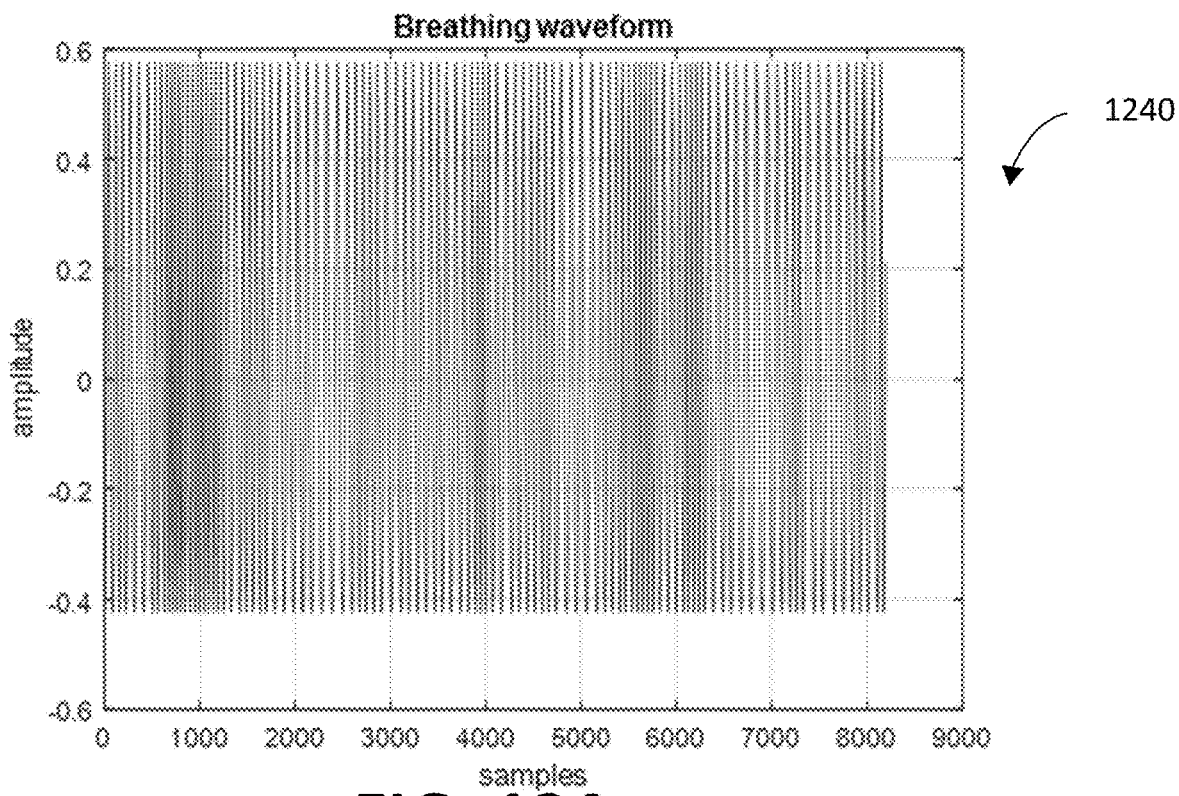
FIGS. 12A-12D show sample graphs illustrating correction of DC or baseline wander performed by a radar-based computing device, according to at least one embodiment.
Figure 12C:
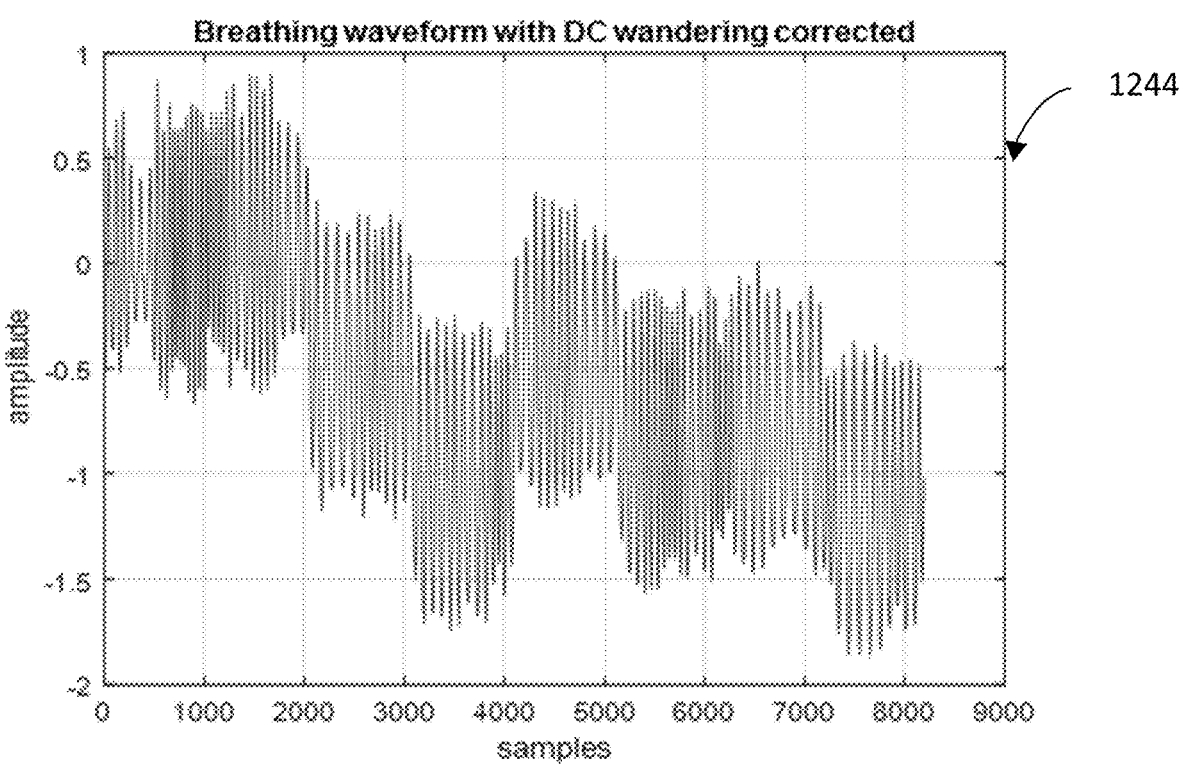
Figure 12D:
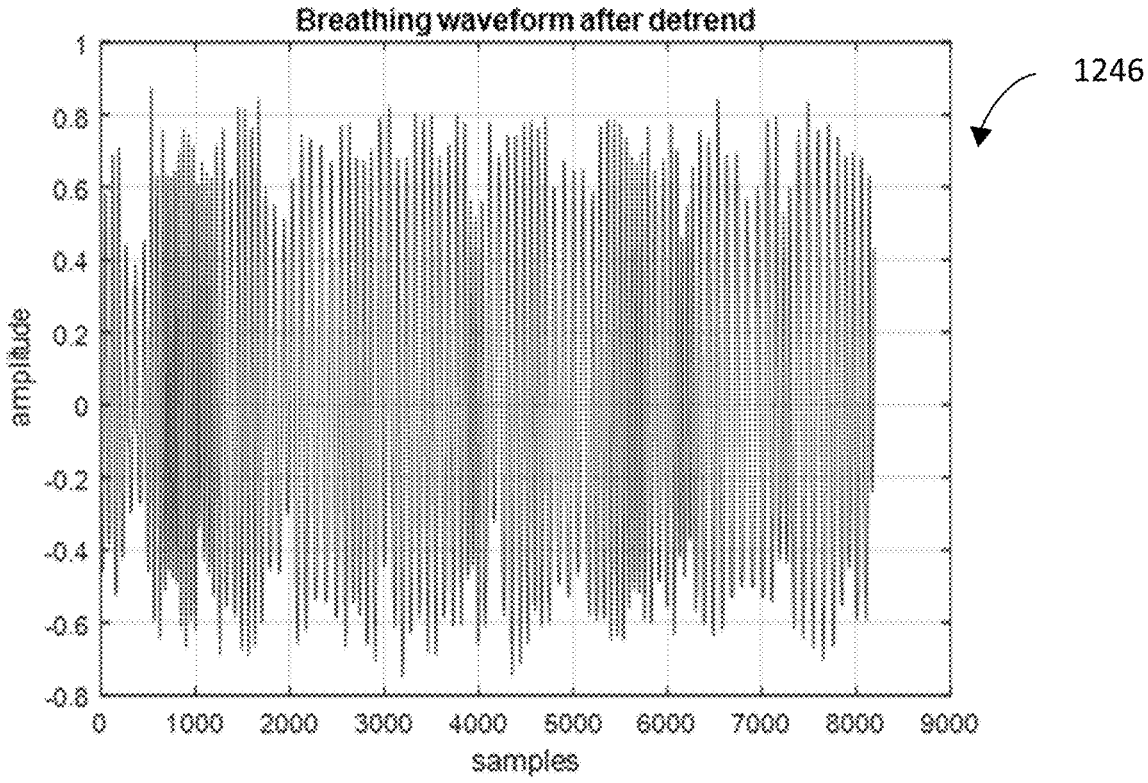

In the first step, a sample window of suitable length is chosen based on the estimated BPM. Moving the median value over the sample window is then subtracted to eliminate any underlying trend. A higher BPM estimate allows a shorter window to be used, and the processing logic chooses the shortest window that results in detrending without distorting the breathing waveform. Another static detrending step removes any residual wandering DC further from the breathing waveform. FIG. 12A illustrates an example breathing waveform 1240. FIG. 12B illustrates an example breathing waveform 1242 impaired with DC wander. FIG. 12C illustrates an example breathing waveform 1244 with DC wandering corrected, and FIG. 12D illustrates an example breathing waveform 1246 after detrending.

Figure 13:
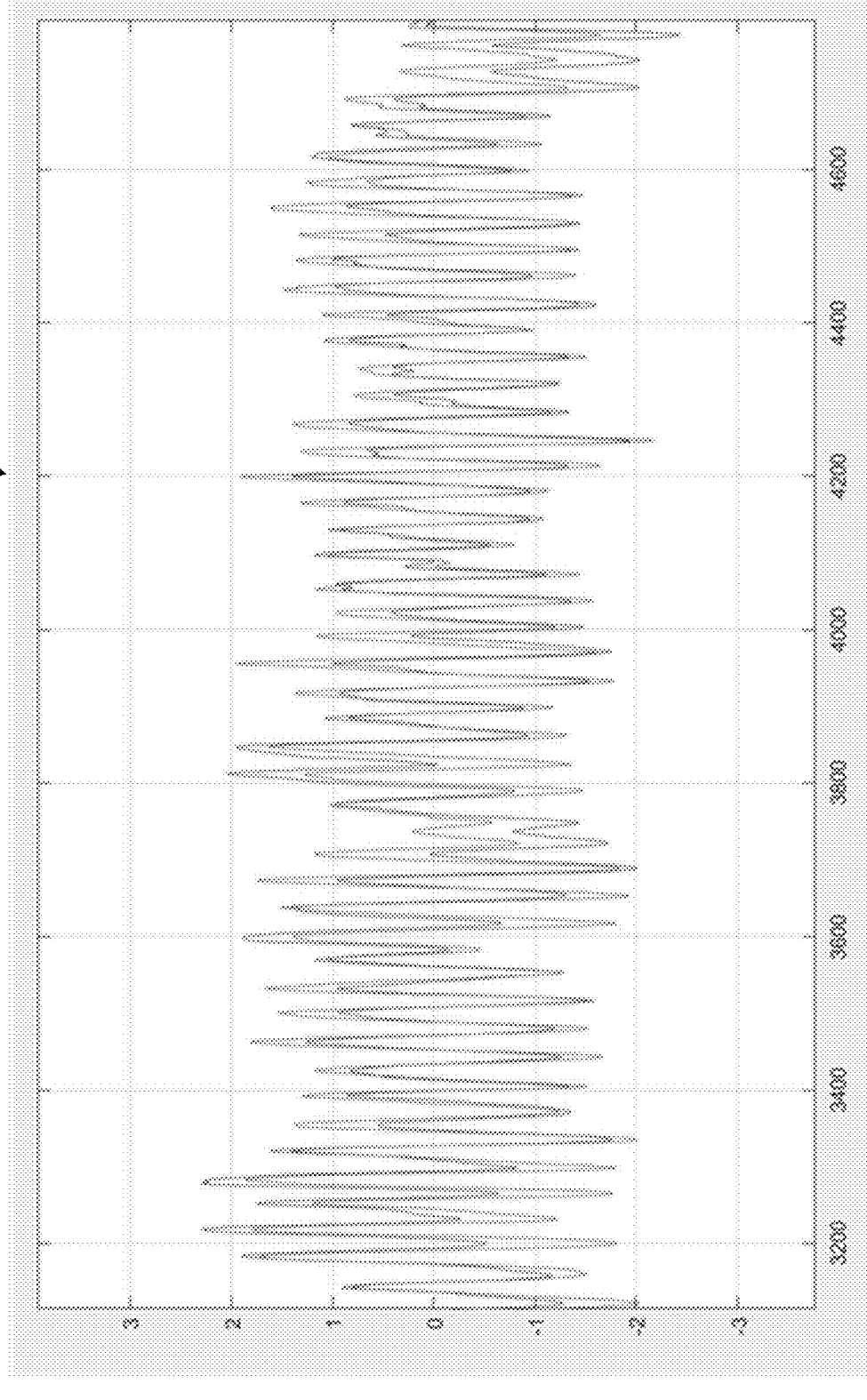
FIG. 13 shows a sample graph illustrating corrected DC or baseline wander in a respiration waveform performed by a radar-based computing device, according to at least one embodiment.

FIG. 13 shows a signal 1300 before and after wandering DC correction. The before signal (dark line) has up and down trends in addition to the respiration signal. This can confuse breathing rate estimation to identify these slow trends as the dominant rate. This issue is resolved with the corrected (lighter line) waveform.

FIG. 14A illustrates example operations in breathing waveform estimation using binning in a method 1400 for monitoring sleep stage of a human in a contactless manner, according to at least one embodiment. More specifically, method 1400 illustrates example operations performed by a device for monitoring a sleep stage of a human in a contactless manner. The device may include a housing, a processor within the housing, and a FMCW radar unit within the housing, which may be coupled to the processor. The method 1400 may be performed by processing logic that may include hardware (circuitry, dedicated logic, etc.), software (such as is run on a general-purpose computer system or a dedicated machine), firmware, or some combination thereof. For example, the method 400 may be performed by the computing device 104, 202, 1200, and particularly by the processor 1262 executing instructions stored in the memory 1340 for performance of aspects of the method 1400. At operation 1402, the processing logic of the computing device may be able to detect, using the FMCW radar unit, the presence of a human within an area of interest of the FMCW radar unit. The area of interest may be a three-dimensional area defined within a field of view of the FMCW radar unit. When the computing device detects a human, the radar unit may transition from a low-power mode to an observational mode. At operation 1404, the processing logic of the computing device may determine, using the FMCW radar unit, that the human is in a first resting position. This may be performed, for example, by analyzing the signals generated by the radar unit. In one example, the signals generated by the radar unit may have a rhythmic waveform pattern (e.g., having periodic peaks and troughs), which may indicate a breathing of a user in the field view of the radar unit. At operation 1406, the processor of the computing device may receive a first waveform of the human resting in the first resting position. At operation 1408, the processor of the computing device may receive a second waveform of the human resting in a second resting position. At operation 1410, the processing logic of the computing device may determine that the first waveform has a higher signal-to-noise ratio (SNR) value than the second waveform, and therefore eliminate the second waveform from further analysis.

FIG. 14B illustrates further operations for polarity compensation and final polarity correction in the method 1400 for monitoring a sleep stage of a human in a contactless manner. These example operations may be performed by a device for monitoring a sleep stage of a human in a contactless manner. At operation 1412, the processing logic of the computing device may determine that the first waveform has a first segment with a first polarity and a second segment with a second polarity. At operation 1414, the processing logic of the computing device may modify the second segment of the first waveform to have the first polarity. At operation 1416, the processing logic of the computing device may determine a phase shift between the first segment and the second segment in the first waveform. The first segment and second segment may be consecutive segments in the first waveform. At operation 1418, the processing logic of the computing device may compensate for the phase shift and stitch/combine the first segment with the second segment to form an intermediate waveform. At operation 1420, the processing logic of the computing device may determine the sleep stage of the human based on the breathing waveform.

In some embodiments, the processor of the computing device may receive a plurality of waveforms, with each waveform having a plurality of segments. The processing logic of the computing device may find a segment circle center in a first segment of a third waveform and offset the first segment from the segment circle center. The processing logic of the computing device may also detrend the first segment with a third-order polynomial. The processing logic of the computing device may further detrend and apply a median filter to the first segment to determine whether the first segment satisfies a predefined criterion. The predefined criterion may include correlating the first segment that is offset by the segment circle center with the first segment offset by a preceding segment circle center to determine whether the first segment has to be inverted. The processing logic of the computing device may, as a result, invert the first segment. In another embodiment, the processing logic of the computing device may determine a correlation value between two or more segments using one of forward windowing, centered windowing, or backward windowing. Responsive to determining that the correlation value is less than a predetermined threshold, the processing logic of the computing device may invert a segment, and stitch/combine segments to form a combined waveform.

In one embodiment, the processing logic of the computing device may divide the combined waveform into a plurality of smaller segments. The processing logic of the computing device may determine a skewness value for each smaller segment in the plurality of smaller segments. For example, a skewness value greater than 1 or less than −1 indicates a highly skewed distribution. A skewness value between 0.5 and 1 or −0.5 and −1 is moderately skewed. A skewness value between −0.5 and 0.5 indicates that the distribution is fairly symmetrical. Responsive to determining that the skewness value of a smaller segment is greater than a predetermined threshold value, the processing logic of the computing device may invert the smaller segment. The predetermined threshold value represents that there is a highly skewed distribution in the segment. In one embodiment, responsive to determining that a motion sensing metric (e.g., whether or not there is motion of an object), a presence sensing metric (e.g., whether or not there is presence of an object), a respiration energy metric (e.g., signal-to-noise ratio), or a coefficient of variation of radius of a third segment is outside of a respective predetermined threshold range, the processing logic of the computing device may delete the third segment and stitching/combining segment immediately preceding the third segment and immediately succeeding the third segment. For example, a large radius indicates a strong reflection from the chest.

Typically, the reflectivity does not change frequently. Therefore, a coefficient of variation in the circle radius indicates a problematic bin. Hence, bins with a larger coefficient of variation (i.e., the ratio of standard deviation to the mean) for the radius are rejected via circle-radius gating. In another embodiment, the processing logic of the computing device may detect a baseline wander in a third waveform and perform a baseline wander correction on the third waveform. In one example, the processing logic of the computing device may determine signal-to-noise ratio values for each waveform over multiple frequency intervals and select a waveform with the highest signal-to-noise ratio value. By applying a correction to the measured waveform, the device may generate a corrected waveform that is more representative of a ground truth breathing waveform, and therefore may allow the computing device or another device to analyze the corrected waveform for sleep stage estimation (e.g., wake, light, deep, or rapid eye movement (REM)) by matching the corrected waveform to known waves associated with a sleep stage. The computing device may use the corrected waveform to determine when a person (e.g., to whom the waveform corresponds) is awake or sleeping, when the person is breathing properly or not breathing, when the person is in particular sleep stages, recommended bedtimes and wake times, and the like. For example, the corrected waveform may be compared to known waveforms associated with different sleep stages (e.g., wake, light, deep, or rapid eye movement (REM)) to identify which sleep stage the user is in currently, and the sleep stage is determined based on the shape of the waveform in the resultant waveform.

Figure 15:
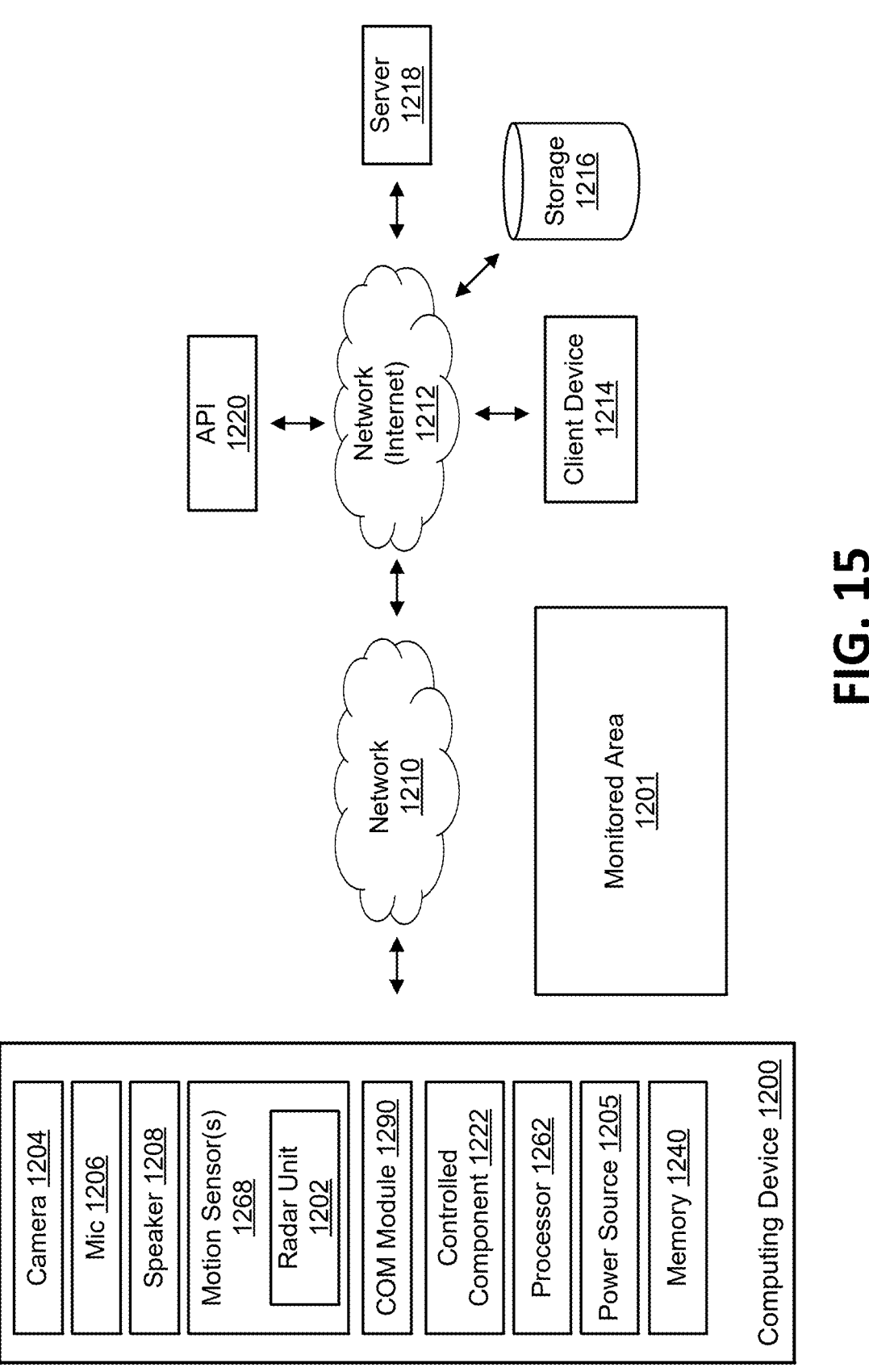
FIG. 15 is a functional block diagram of a computing device for monitoring sleep stage of a human in a contactless manner, according to at least one embodiment.

FIG. 15 is a functional block diagram of a computing device 1200, according to at least one embodiment. The computing device 1200 may include the camera 1204, a power source 1205, a microphone 1206, a speaker 1208, at least one controlled component 1222, a memory 1240, the processor 1262, one or more motion sensors 1268 (including the radar unit 1202), and a communication module 1290. The controlled component 1222 may include, but is not limited to, a doorbell, an internal floodlight, an external floodlight, or another security device. The computing device 1200 may be configured to monitor a monitored area 1201. The processor 1262 may include, and may also be referred to as, a controller or a microcontroller, and may include multiple processors in some embodiments. In another embodiment, the processor 1262 can be coupled to other medical devices, such as a CPAP machine, via one or more links. In an example mode of operation, the computing device 1200 communicates with a wireless network 1210 of a user. Although the wireless network 1210 is referred to herein as "wireless," in some embodiments may not be wireless, such as where the computing device 1200 is connected to the user's network via an Ethernet connection, for example. The wireless network 1210 is connected to another network 1212. The networks 1210 and 1212 may be the same network, in some of the present embodiments. The networks 1210 and 1212 may include but are not limited to the Internet, a Wi-Fi network compatible with the IEEE 802.11 standard, and/or other wireless communication standard(s) may include but are not limited to WAP (Wireless Application Protocol), GPRS (General Packet Radio Service), GSM (Global System for Mobile Communication), LTE, VOLTE, LoRaWAN, LPWAN, RPMA, LTE Cat-"X" (e.g., LTE Cat 1, LTE Cat 0, LTE CatM1, LTE Cat NB1), CDMA (Code Division Multiple Access), TDMA (Time Division Multiple Access), FDMA (Frequency Division Multiple Access), and/or OFDMA (Orthogonal Frequency Division Multiple Access) cellular phone networks, GPS, CDPD (cellular digital packet data), Z-Wave, RIM (Research in Motion, Limited) duplex paging network, Bluetooth radio, an IEEE 802.11-based radio frequency network, or a combination thereof.

As described below, the computing device 1200 may communicate with a client device 1214 of the user via the wireless network 1210 and/or the network 1212. The client device 1214 may include, for example, a computer, a laptop, a tablet, a mobile telephone (may also be referred to as a cellular telephone), such as a smartphone, a personal digital assistant (PDA), or another computing device capable of receiving and/or transmitting data across one or both of the networks 1210, 1212. The client device 1214 may include a display (e.g., a user interface (display)) and related components capable of displaying streaming and/or recorded video images. The client device 1214 may also include a speaker and related components capable of broadcasting streaming and/or recorded audio, and may also include a microphone.

The computing device 1200 may also communicate with one or more remote storage device(s) 1216, one or more servers 1218, and/or an application programming interface (API) 1220 via the wireless network 1210 and the network 1212 (Internet/PSTN). While FIG. 15 illustrates the remote storage device 1216, the server 1218, and the API 1220 as components separate from the network 1212, it is to be understood that the remote storage device 1216, the server 1218, and/or the API 1220 may be considered to be components of the network 1212.

The API 1220 may include, for example, a server (e.g., a bare-metal server, or a virtual machine, or a machine running in a backend infrastructure as a service), or multiple servers networked together, exposing at least one API to client(s) accessing it. These servers may include components such as application servers (e.g., software servers), depending upon what other components are included, such as a caching layer, or database layers, or other components. The API 1220 may, for example, include many such applications, each of which communicates with one another using their public APIs. In some embodiments, the API 1220 may hold the bulk of the user data and offer the user management capabilities, leaving the clients to have a very limited state.

The API 1220 may include one or more APIs. An API is a set of routines, protocols, and tools for building software and applications. An API expresses a software component in terms of its operations, inputs, outputs, and underlying types, defining functionalities that are independent of their respective implementations, which allows definitions and implementations to vary without compromising the interface. Advantageously, an API may provide a programmer with access to an application's functionality without the programmer needing to modify the application itself, or even understand how the application works. An API may be for a web-based system, an operating system, or a database system, and it provides facilities to develop applications for that system using a given programming language. In addition to accessing databases or computer hardware like hard disk drives or video cards, an API can ease the work of programming GUI components. For example, an API can facilitate the integration of new features into existing applications (a so-called "plug-in API"). An API can also assist otherwise distinct applications with sharing data, which can help to integrate and enhance the functionalities of the applications.

In various embodiments, the API 1220 includes one or more services (also referred to as network services). A network service is an application that provides data storage, manipulation, presentation, communication, and/or other capabilities. Network services are often implemented using a client-server architecture based on application-layer network protocols. Each service may be provided by a server component running on one or more computers (such as a dedicated server computer offering multiple services) and accessed via a network by client components running on other devices. However, the client and server components can both be run on the same machine. Clients and servers may have a user interface, and sometimes other hardware associated with them.

The memory 1240 may be transitory and/or non-transitory and may represent one or both of volatile memory (e.g., SRAM, DRAM, computational RAM, other volatile memory, or any combination thereof) and non-volatile memory (e.g., FLASH, ROM, magnetic media, optical media, other non-volatile memory, or any combination thereof). Part or all of the memory 1240 may be integrated with the processor 1262.

Figure 16:
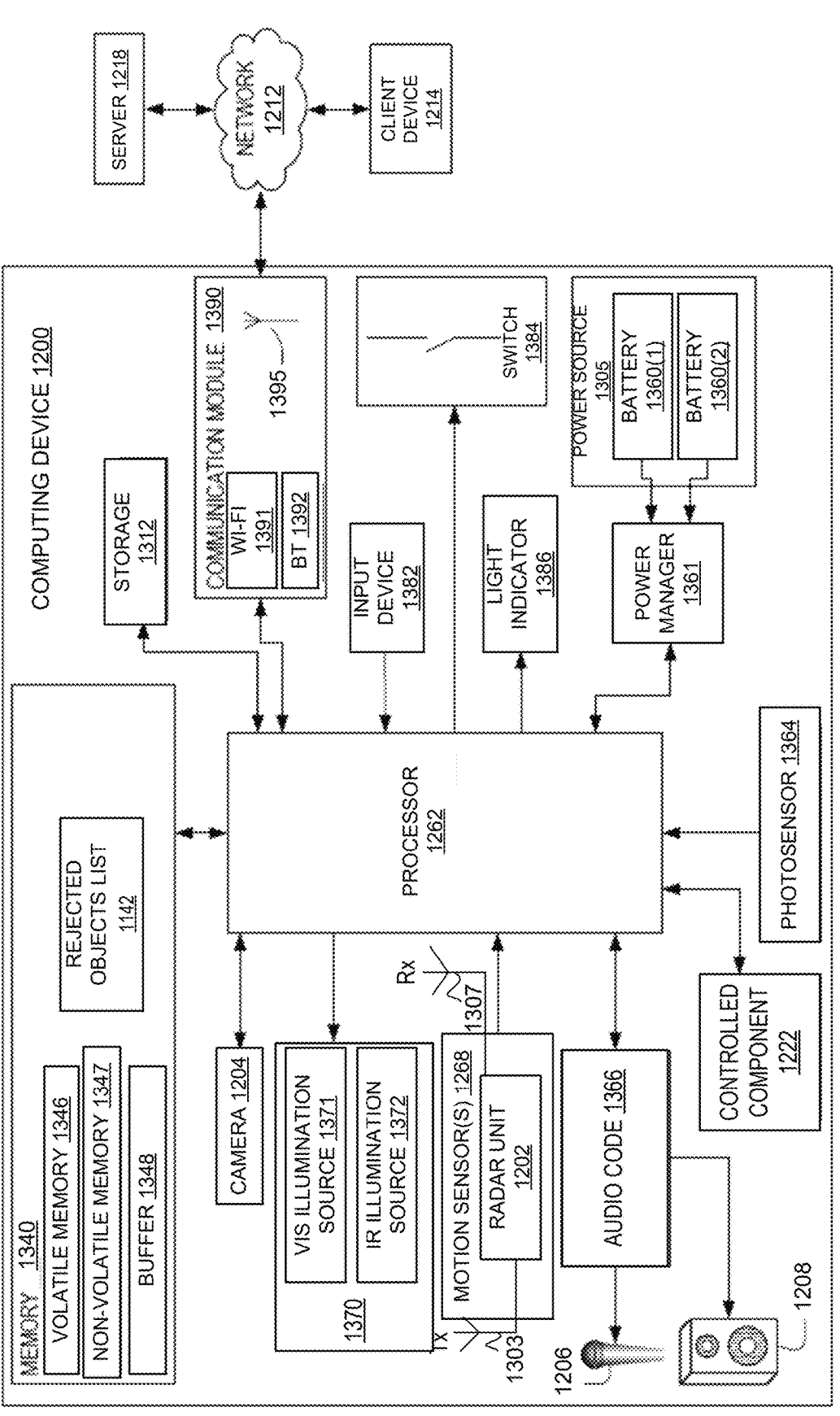
FIG. 16 is a functional block diagram of a more-detailed example of a computing device of FIG. 15, according to at least one embodiment.

FIG. 16 is a functional block diagram illustrating components of a more-detailed example of a computing device 1200, which is an embodiment of the computing device 104 of FIG. 1 and computing device 202 of FIG. 2. In various embodiments, the computing device 1200 includes a power source 1305, a memory 1340, and a communication module 1390, which are examples of the power source 1205, the memory 1240, and the communication module 1290, respectively, of the computing device 1200. An embodiment of the computing device 1200 may also include the controlled component 1222, a housing 1301 to encapsulate the majority of the illustrated components, a photosensor 1364, an audio codec 1366, an illumination source 1370, an input device 1382, a light indicator 1386, each of which, when included, may be communicatively coupled to the processor 1262, which will be discussed.

The computing device 1200 may also include a power manager 1361. The power source 1305 includes at least two batteries 1360(1) and 1360(2), in some of the present embodiments. However, in other embodiments, the power source 1305 may include more or fewer batteries, including zero batteries if the power source 1305 is hardwired to an electrical power source of a structure to which the computing device 1200 is mounted. In alternative embodiments, the batteries 1360(1) and 1360(2) are fuel cells, solar arrays, or other low voltage power sources. Each of the batteries 1360(1) and 1360(2) may be electrically connected to the power manager 1361. The audio codec 1366 may drive the speaker 1208 and receive input from the microphone 1206. The illumination source 1370 may include a visible illumination source 1371 and an infrared illumination source 1372. The input device 1382 may be, for example, a button, an electrical switch, and/or a manually operated electromechanical device.

The power manager 1361 manages the power source 1305 to provide electrical power to operate the computing device 1200, as described below. The power manager 1361 may include an electronic circuit that operates to condition power from the batteries 1360 and to select from which of the batteries 1360(1) and 1360(2) (in embodiments with more than one battery) power is drawn. For example, the power manager 1361 may draw power from the battery 1360(1), and may switch to draw power from the battery 1360(2) when the battery 1360 (1) is drained. By drawing power from only one of the batteries 1360 at a time, the computing device 1200 may continue operation when the depleted one of the batteries 1360 is removed for recharging. In some embodiments, the computing device 1200 may further include a switch 1384 controlled by the processor 1262 to activate the external illumination source 1370.

The processor 1262 may perform data processing and various other functions of the computing device 1200, as described below. The memory 1340 may include volatile memory 1346 and non-volatile memory 1347. In some embodiments, the processor 1262, the volatile memory 1346, the non-volatile memory 1347, and/or programmable input/output peripherals (not shown) may be configured as an integrated circuit. The volatile memory 1346 may be implemented as DDR3 or DDR4 SDRAM (double data rate type three or four synchronous dynamic random-access memory) or the like future generation memory. The non-volatile memory 1347 may be implemented as NAND flash memory. The memory 1340 may store instructions, that when executed by at least one processor, such as the processor 1262, cause the disclosed video recording and computing device to perform functions in relation to the operation of the components coupled to the processor 1262.

Although the volatile memory 1346 and the non-volatile memory 1347 are shown outside the box representing the processor 1262 in the example of FIG. 16, in some embodiments, the volatile memory 1346 and/or the non-volatile memory 1347 may be physically incorporated with the processor 1262, such as on the same integrated circuit (chip). The volatile memory 1346 and/or the non-volatile memory 1347, regardless of their physical location, may be shared by one or more other components (in addition to the processor 1262) of the computing device 1200. In certain embodiments, the computing device 1200 includes additional storage 1312 that may be implemented as any type of non-volatile data storage, such as, for example, and without limitation, hard disks/drives, flash memory, or any other suitable memory/storage element. In some embodiments, the non-volatile memory 1347 and the additional storage 1312 may be combined as a single non-volatile memory. The additional storage 1312, when included, may be operatively connected to the processor 1262 and may be used to store audio and/or video information captured by the computing device 1200, as described in further detail below.

In some embodiments, the camera 1204 and the infrared illumination source 1372 may cooperate to facilitate the night vision functionality of the computing device 1200. For example, the photosensor 1364 may be configured to detect a level of ambient light about the computing device 1200. The processor 1262 may use the input from the photosensor 1364 to control the operation of the infrared illumination source 1372 and the camera 1204 to activate and deactivate night vision, as described in further detail below. In some embodiments, the camera 1204 may include a video recording sensor or a camera chip. In some embodiments, the infrared illumination source 1372 may include one or more IR light-emitting diodes (LEDs).

The transfer of digital audio between the user (via the user's client device 1214) and a visitor (or intruder) may be compressed and decompressed using the audio codec 1366, as described below. The motion sensor 1268 may include the radar unit 1202 and optionally include one or more passive infrared (PIR) sensors or other types of sensors capable of detecting and communicating to the processor 1262 the presence and/or motion of an object within its field of view. When triggered by the motion sensor 1268, the processor 1262 may perform one or more functions, as described below.

In various embodiments, the radar unit 1202 is designed with different types of radar, including but not limited to FMCW radar, pulse or pulse-Doppler radar, or a combination of one or more of these radar types. Thus, the radar unit
1202 may be a frequency-modulated continuous wave radar
unit, a pulse radar unit, or a combination of the two, as will
be discussed in more detail. Different types of frequency
modulated (FM) radar may be referred to jointly as FM
radar. The computing device 1200 may further include, or be
coupled to, one or more radar antenna, including at least one
transmit antenna 1303, coupled to a transmitter (Tx), in
order to transmit radar signals, and one or more receive
antenna 1307, coupled to a receiver (Rx), to receive reflected
radar signals. In one embodiment, the transmitter and
receiver are combined and are simply referred to as a
receiver.

In various embodiments, the FMCW radar, also referred
to as continuous-wave frequency-modulated (CWFM) radar,
is a short-range measuring radar set capable of determining
distance, but also adaptable to include Doppler and thus the
ability to measure the speed of a moving object, which aids
in identifying objects. The distance measurement, along
with the speed measurement, increases reliability when there
is more than one source of reflection arriving at the radar
antenna. In FMCW radar, the transmitted signal of a known
stable frequency continuous wave varies up and down in
frequency over a fixed period of time by a modulating
signal. The frequency difference between the receive signal
and the transmit signal increases with delay, and hence with
distance. This smears out, or blurs, the Doppler signal.
Reflections (or echoes) received back from a target are then
mixed with the transmitted signal to produce a beat signal,
which will give the distance of the target after demodulation.

The modulations possible in FMCW vary, so long as
frequency varies, including but not limited to a sine wave
(like an air raid siren), a sawtooth wave (like a chirp from
a bird), a triangle wave (like a police siren in the United
States), or a square wave (like a siren in the United King-
dom). Sawtooth modulation is the most used in FMCW
radars, where the range is desired for objects that may lack
rotating parts. Range information is mixed with the Doppler
velocity using this technique. Modulation can be turned off
during alternate scans to identify velocity using unmodu-
lated carrier frequency shift. This allows range and velocity
to be found with one radar set. Triangle wave modulation
can be used to achieve the same goal. Sinusoidal FM may be
used when both range and velocity are desired simultane-
ously for complex objects with multiple moving parts like
turbine fan blades, helicopter blades (including as on a
drone), or propellers. This processing reduces the effect of
complex spectra modulation produced by rotating parts that
introduce errors into the range measurement process. For
simplicity of explanation, all of these waveform FM types
will be referred to as "chirps," meaning a cycle of a radar
signal that changes in frequency throughout a period of time
before repeating.

In various embodiments, operational parameters of
FMCW radar may be adjusted to vary the amount of power
consumed. These operational parameters include, but are not
limited to, chirps per frame, frame per second (or frame
rate), antenna configuration (e.g., number of active receive
antennas being used), chirp duration, and the various digital
signal processing (DSP) or central processing unit (CPU)
functions employed to process received radar signals. In
some embodiments, each radar unit 1202 may include a
digital signal processor and at least one CPU, e.g., a pro-
cessing core, to perform these functions. In other embodi-
ments, the digital signal processor is located off-package of
the radar unit 1202 and may be located elsewhere on the
computing device 1200, including possibly integrated within the processor 1262. Regardless of where located, the radar
unit 1202, as is referenced herein, is assumed to include the
digital signal processor and at least one CPU core.

In the disclosed embodiments, as discussed, a frame may
be understood to be a period of time during which the radar
unit 1202 samples the monitored area 1201 to capture a
dataset capable of being processed by one or more process-
ing functions to perform object detection. As such, each
frame may include multiple chirps in order to capture
sufficient data for object detection processing. The DSP/
CPU functions include, but are not limited to, stationary
object removal, range Fast Fourier Transform (FFT) pro-
cessing, amplitude thresholding, angle of arrival estimation,
and Doppler FFT processing.

Stationary object removal is a process of subtracting one
frame (or a combination of previous frames) from the
current frame to remove any unchanging signals from the
data. An object that has not moved will be zeroed out by
doing this. The goal is to only look at objects moving in
space across time.

Range FFT is the process of running the intermediate
frequency (IF, the mixture of the transmitted signal with the
incoming reflected signal) through an FFT to convert the
received frequencies into distances. Ultimately, the time
delay of each reflected signal is what translates into a
frequency, and the FFT translates this into a superposition of
distances. Each distance will have some amplitude associ-
ated with it depending on how strong the received signal was
from that target.

Amplitude thresholding is the process of setting some
threshold above the measured background noise, and seeing
if the amplitudes of received signals exceed that threshold.
If exceeding, then a detection is possible.

The angle of Arrival (AoA) estimation may involve the
triangulation of reflected signals to determine an angle at
which the reflected signals are arriving. When multiple
receive antennas 1307 are enabled, it is possible to compare
the phase data from each receiver coupled to the respective
receive antenna. Depending on the spatial separation of
these receive antennas (distance and plane of separation), the
radar unit 1202 may locate not only the distance of the
targets, but also the angle from which the reflection arrived
at the radar unit 1202. This allows the localization of an
object in two-dimensional (2D) or three-dimensional (3D)
space rather than just a single-dimensional distance.

With reference to Doppler FFT, when multiple chirps are
enabled, the radar unit 1202 may perform a second FFT on
received frames of data to resolve not only the distances of
objects (from the first FFT), but also the speed at which the
objects are moving (from the second FFT). This is more
accurate than deducing the speed of objects by measuring
distance/time throughout multiple frames. Use of the Dop-
pler FFT may enable determining an identity of a detected
object, such as resolving that the object detected is a human,
not a cat or a leaf.

In various embodiments, a pulse radar is a radar system
that employs a repetitive series of short-duration pulses that
make up a larger pulse. Each larger pulse may thus define a
pulse width or a pulse duration. A pulse repetition period,
e.g., the period between each large pulse, may define a pulse
rate, e.g., the number of large pulses per second. Each pulse
in the series of short-duration pulses may be a different kind
of wave, such as was discussed with reference to FMCW
radar (sine, sawtooth, triangle, or square), but, different from
FMCW radar, are not continuous and do not change in
frequency (unless using pulse-Doppler radar). The reflected radar signals, from the transmitted radar pulses, may be processed in order to determine distance.

In disclosed embodiments, the range accuracy of a pulse radar depends on the width of the pulse: the shorter the pulse, the better the accuracy. Short pulses, however, require wide bandwidths in the receiver and transmitter (since bandwidth is equal to the reciprocal of the pulse width). The bandwidth (BW) is the difference between the upper and lower cut-off frequencies of the transmitter and receiver, and is usually measured in hertz (Hz). The larger the bandwidth of the transmitter, the shorter the rise time of the edges of a rectangular pulse, for example. A radar with a pulse width of one microsecond can measure the range to an accuracy of a few tens of meters or better.

Since a pulse radar does not radiate continually, the average power is much less than the peak power. The average power, rather than the peak power, is the measure of the capability of a radar system. Radars have average powers from a few milliwatts (mW) to as much as one or more megawatts (MW), depending on the application. A pulse radar will consume more power at a higher bandwidth, thus lower pulse width, and at higher frequencies, thus higher pulse rates.

In some embodiments, a pulse-Doppler radar is a radar system that determines the range of a target using pulse-timing techniques, and uses the Doppler effect of the returned signal to determine the velocity of the target object. Further, the application of the Doppler FFT on the returned signals may enable distinguishing objects from each other and enable identification of the target object. Thus, pulse-Doppler radar may be especially adept at distinguishing higher-speed objects (e.g., a sprinting person or a motor vehicle) in close proximity to large slow-moving objects, such as trees or bodies of water. Pulse-Doppler radar may thus combine the features of pulse radars and continuous-wave radars, which were formerly separate due to the complexity of the electronics.

The memory 1340 may further include a rejected objects list 1142, a buffer 1348, and, in certain embodiments, may also include the volatile memory 346 and/or the non-volatile memory 1347. The buffer 1348 may be part of the volatile memory 1346 and/or the non-volatile memory 1347. The buffer 1348 may be a rolling buffer such as a circular buffer, a circular queue, a cyclic buffer, a ring buffer, or other data structures that use a single, fixed-size buffer as if it were connected end-to-end. Video from camera 1204 may be stored in the buffer 348 in response to a certain trigger, such as when the computing device 1200 transitions the radar unit 1202 from the first operational mode or the second operational mode to the second operational mode or the third operational mode, respectively, in response to certain types of motion detection, as will be discussed in more detail.

The communication module 1390 includes at least one antenna 1395, and is configured to handle communication between the computing device 1200 and other, external devices or receivers, and to route incoming/outgoing data appropriately. For example, inbound data from the antenna 1395 may be routed through the communication module 1390 before being directed to the processor 1262, and outbound data from the processor 1262 may be routed through the communication module 1390 before being directed to the antenna 1395. The communication module 390 may include one or more transceiver modules capable of transmitting and receiving data, and using, for example, one or more protocols and/or technologies, such as a Wi-Fi network compatible with the IEEE 802.11 standard and/or other wireless communication standard(s) including but not limited to WAP (Wireless Application Protocol), GPRS (General Packet Radio Service), GSM (Global System for Mobile Communication), LTE, VOLTE, LoRaWAN, LPWAN, RPMA, LTE Cat-"X" (e.g., LTE Cat 1, LTE Cat 0, LTE CatM1, LTE Cat NB1), CDMA (Code Division Multiple Access), TDMA (Time Division Multiple Access), FDMA (Frequency Division Multiple Access), and/or OFDMA (Orthogonal Frequency Division Multiple Access) cellular phone networks, GPS, CDPD (cellular digital packet data), Z-Wave, RIM (Research in Motion, Limited) duplex paging network, Bluetooth radio, or an IEEE 802.11-based radio frequency network or any other protocol and/or technology. In the illustrated embodiment, the communication module 1390 may include a Wi-Fi chip 1391 and a Bluetooth chip 1392 that implement medium-range wireless communication protocols and short-range wireless communication protocols, respectively, but these components are merely examples and are not limiting. Further, while the Wi-Fi chip 1391 and the Bluetooth chip 1392 are illustrated within the box representing the communication module 390, the embodiment illustrated in FIG. 16 is merely an example, and, in some embodiments, the Wi-Fi chip 1391 and/or the Bluetooth chip 1392 may not necessarily be physically incorporated with the communication module 1390.

In some embodiments, the communication module 1390 may further include a wireless repeater (not shown and may also be referred to as a wireless range extender). The wireless repeater may be configured to receive a wireless signal from a wireless router (or another network device) in the user's wireless network 1210 and rebroadcast the signal. Wireless devices that are not within the broadcast range of the wireless router, or that only weakly receive the wireless signal from the wireless router, may receive the rebroadcast signal from the wireless repeater of the communication module 1390, and may thus connect to the user's wireless network 1210 through the computing device 1200. In some embodiments, the wireless repeater may include one or more transceiver modules (not shown) capable of transmitting and receiving data, and using, for example, one or more medium-range wireless communication protocols and/or technologies, such as Wi-Fi (IEEE 802.11), long-range wireless communication protocols, such as WiMAX (IEEE 802.16), or any other protocol and/or technology.

The input device 1382 may have one or more functions, such as changing an operating mode of the computing device 1200 and/or triggering a reset of the computing device 1200. For example, when the input device 382 is activated (e.g., pressed and released), it may cause the communication module 1390 of the computing device 1200 to enter an access point (AP) mode, which may facilitate connecting the computing device 1200 to the user's wireless network 1210 and/or the network 1212. Alternatively, or in addition, when the input device 1382 is activated (e.g., pressed and held) for at least a threshold amount of time, it may trigger the erasing of any data stored by the volatile memory 346 and/or by the non-volatile memory 1347, and/or may trigger a reboot of the processor 1262.

Some portions of the detailed description are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to the desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, as apparent from the above discussion, it is appreciated that throughout the description, discussions utilizing terms such as "radiating," "detecting," "determining," "generating," "communicating," "receiving," "disabling," or the like, refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices.

Embodiments also relate to an apparatus for performing the operations herein. This apparatus may be specially constructed for the required purposes, or it may comprise a general-purpose computer selectively activated or reconfigured by a computer program stored in the computer. Such a computer program may be stored in a non-transitory computer-readable storage medium, such as, but not limited to, any type of disk, including floppy disks, optical disks, CD-ROMs and magnetic-optical disks, read-only memories (ROMs), random access memories (RAMs), Electrically Programmable ROMs (EPROMs), Electrically Erasable Programmable ROMs (EEPROMs), magnetic or optical cards, or any type of media suitable for storing electronic instructions.

The algorithms and displays presented herein are not inherently related to any particular computer or other apparatus. Various general-purpose systems may be used with programs in accordance with the teachings herein, or it may prove convenient to construct a more specialized apparatus to perform the required method steps. The required building for a variety of these systems will appear in the description below. In addition, the present embodiments are not described with reference to any particular programming language. It will be appreciated that a variety of programming languages may be used to implement the teachings of the present embodiments as described herein. It should also be noted that the terms "when" or the phrase "in response to," as used herein, should be understood to indicate that there may be intervening time, intervening events, or both before the identified operation is performed.

As used herein, the phrases "at least one of A, B and C," "at least one of A, B, or C," and "A, B, and/or C" are synonymous and mean logical "OR" in the computer science sense. Thus, each of the foregoing phrases should be understood to read on (A), (B), (C), (A and B), (A and C), (B and C), and (A and B and C), where A, B, and C are variables representing elements or features of the claim. Also, while these examples are described with three variables (A, B, and C) for ease of understanding, the same interpretation applies to similar phrases in these formats with any number of two or more variables.

The above description presents the best mode contemplated for carrying out the present embodiments, and of the manner and process of practicing them, in such full, clear, concise, and exact terms as to enable any person skilled in the art to which they pertain to practice these embodiments.

The present embodiments are, however, susceptible to modifications and alternate constructions from those discussed above that are fully equivalent. Consequently, the present invention is not limited to the particular embodiments disclosed. On the contrary, the present invention covers all modifications and alternate constructions coming within the spirit and scope of the present disclosure. For example, the steps in the processes described herein need not be performed in the same order as they have been presented, and may be performed in any order(s). Further, steps that have been presented as being performed separately may in alternative embodiments be performed concurrently. Likewise, steps that have been presented as being performed concurrently may in alternative embodiments be performed separately.

What is claimed is:

1. An electronic device comprising:

at least one processor;

a radar unit communicatively coupled with the at least one processor; and a memory storing instructions that, when executed by the at least one processor, cause the electronic device to:

detect a presence of a human within an area of interest of the radar unit;

receive a first dataset indicative of the human resting in a first position;

receive a second dataset indicative of the human resting in the first position;

determine that the first dataset has a higher signal-to-noise ratio value than the second dataset;

determine that the first dataset includes a first portion that has a first polarity and a second portion that has a second polarity;

modify the second portion to have the first polarity to generate a modified first dataset;

determine a phase shift between the first portion and the second portion and compensate for the phase shift, wherein the first portion and second portion are consecutive portions;

combine the first portion with the second portion to form a combined first dataset; and determine a sleep stage associated with the human based on a shape of the combined first dataset, wherein determining the sleep stage comprises comparing the shape of the combined first dataset to known waveforms that are associated with different sleep stages.

2. The electronic device of claim 1, the memory storing further instructions that, when executed by the at least one processor, further cause the electronic device to:

receive a third dataset;

determine a segment circle center in a first segment of the third dataset;

offset the first segment from the segment circle center;

detrend the first segment with a third order polynomial;

detrend and apply a median filter to the first segment;

determine the first segment satisfies a predefined criterion; and invert the first segment.

3. The electronic device of claim 2, wherein determining the first segment satisfies the predefined criterion further comprises correlating the first segment that is offset by the segment circle center with a first segment offset by a preceding segment circle center to determine the first segment has to be inverted.

4. The electronic device of claim 1, the memory storing further instructions that, when executed by the at least one processor, further cause the electronic device to:

determine a correlation value between a fourth dataset and a fifth dataset using one of forward windowing, centered windowing, or backward windowing;

responsive to determining that the correlation value is less than a predetermined threshold, invert the fifth dataset; and combine the fourth dataset and the fifth dataset to form a combined dataset.

5. The electronic device of claim 4, the memory storing further instructions that, when executed by the at least one processor, further cause the electronic device to:

divide the combined dataset into a plurality of segments;

determine a skewness value for each segment in the plurality of segments; and responsive to determining that the skewness value of a first segment is greater than a predetermined threshold value, invert the first segment.

6. The electronic device of claim 1, the memory storing further instructions that, when executed by the at least one processor, further cause the electronic device to: responsive to determining that a motion sensing metric, a presence sensing metric, a respiration energy metric, or a coefficient of variation of radius of a sixth dataset is outside of a respective predetermined threshold range, deleting the sixth dataset and combining a segment immediately preceding the sixth dataset and a segment immediately succeeding the sixth dataset.

7. The electronic device of claim 1, wherein the at least one processor, the radar unit, and the memory are located in a housing.

8. A method comprising:

operating a radar unit of an electronic device;

receiving, by a processor coupled to the radar unit, a first dataset of a human resting in a first resting position;

receiving a second dataset of the human resting in the first resting position;

determining the first dataset has a higher signal-to-noise ratio value than the second dataset;

determining that the first dataset has a first segment that has a first polarity and a second segment that has a second polarity;

modifying the second segment of the first dataset to have the first polarity;

determining, by the processor, a phase shift between the first segment and the second segment in the first dataset, wherein the first segment and second segment are consecutive segments in the first dataset;

compensating for the phase shift and combining the first segment with the second segment to form a combined dataset; and determining a sleep stage of the human based on a shape of the combined dataset, wherein determining the sleep stage comprises comparing the shape of the combined dataset to known waveforms that are associated with different sleep stages.

9. The method of claim 8, further comprising:

receiving, by the processor, a third dataset;

finding a segment circle center in a first segment of the third dataset;

offsetting the first segment of the third dataset from the segment circle center;

detrending the first segment of the third dataset with a third order polynomial;

detrending and applying a median filter to the first segment of the third dataset;

determining the first segment of the third dataset satisfies a predefined criterion; and inverting the first segment of the third dataset.

10. The method of claim 9, wherein determining the first segment of the third dataset satisfies the predefined criterion further comprises correlating the first segment of the third dataset that is offset by the segment circle center with a first segment offset by a preceding segment circle center to determine the first segment of the third dataset has to be inverted.

11. The method of claim 8, further comprising:

determining, by the processor, a correlation value between a fourth dataset and a fifth dataset using one of forward windowing, centered windowing, or backward windowing;

responsive to determining that the correlation value is less than a predetermined threshold, inverting the fifth dataset; and combining the fourth dataset and the fifth dataset to form a combined dataset.

12. The method of claim 11, further comprising:

dividing, by the processor, the combined dataset into a plurality of segments;

determining a skewness value for each segment in the plurality of segments; and responsive to determining that the skewness value of a first segment of the combined dataset is greater than a predetermined threshold value, inverting the first segment of the combined dataset.

13. The method of claim 8, further comprising:

responsive to determining that a motion sensing metric, a presence sensing metric, a respiration energy metric, or a coefficient of variation of radius of a sixth dataset is outside of a respective predetermined threshold range, deleting the sixth dataset and combining a segment immediately preceding the sixth dataset and a segment immediately succeeding the sixth dataset.

14. The method of claim 8, further comprising:

detecting a baseline DC wander in a seventh dataset;

modifying the seventh dataset to correct the baseline DC wander;

determining signal-to-noise ratio values for each dataset over multiple frequency intervals; and selecting a dataset with the highest signal-to-noise ratio value.

15. An electronic device comprising:

a housing;

a processor within the housing; and a pulsed radar unit within the housing and coupled to the processor;

a memory operatively coupled to the processor, the memory storing instructions that, when executed by the processor, cause the electronic device to:

receive a first dataset indicative of a human resting in a first position;

receive a second dataset indicative of the human resting in the first position;

determine that the first dataset has a higher signal-to-noise ratio value than the second dataset;

determine that the first dataset includes a first portion that has a first polarity and a second portion that has a second polarity;

modify the second portion to have the first polarity to generate a modified first dataset;

determine a phase shift between the first portion and the second portion and compensate for the phase shift, wherein the first portion and second portion are consecutive portions; and combine the first portion with the second portion to form a combined first dataset; and determine a sleep stage associated with the human based on a shape of the combined first dataset, wherein determining the sleep stage comprises comparing the shape of the combined first dataset to known waveforms that are associated with different sleep stages.

16. The electronic device of claim 15, the memory storing further instructions that, when executed by the processor, further cause the electronic device to:

receive a third dataset;

determine a segment circle center in a first segment of the third dataset;

offset the first segment from the segment circle center;

detrend the first segment with a third order polynomial;

detrend and apply a median filter to the first segment;

determine the first segment satisfies a predefined criterion; and invert the first segment.

17. The electronic device of claim 15, the memory storing further instructions that, when executed by the processor, further cause the electronic device to:

determine a correlation value between a fourth dataset and a fifth dataset using one of forward windowing, centered windowing, or backward windowing;

responsive to determining that the correlation value is less than a predetermined threshold, invert the fifth dataset; and combine the fourth dataset and the fifth dataset to form a combined dataset.

* * * * *